United States Patent [19]

Satomura et al.

[11] Patent Number: 4,837,450
[45] Date of Patent: Jun. 6, 1989

[54] APPARATUS FOR READING A FILM IMAGE WITH CONTROLLABLE ILLUMINATION AND THRESHOLD VALUE

[75] Inventors: Seiichiro Satomura, Kawasaki; Masahide Kotera, Yokohama, both of Japan

[73] Assignee: Canon Kabushiki Kaisha, Tokyo, Japan

[21] Appl. No.: 259,414

[22] Filed: Oct. 18, 1988

Related U.S. Application Data

[63] Continuation of Ser. No. 191,837, May 2, 1988, abandoned, which is a continuation of Ser. No. 878,790, Jun. 26, 1986, abandoned.

[30] Foreign Application Priority Data

| Jul. 1, 1985 | [JP] | Japan | 60-144219 |
| Jul. 1, 1985 | [JP] | Japan | 60-144221 |
| Jul. 1, 1985 | [JP] | Japan | 60-144223 |
| Jul. 1, 1985 | [JP] | Japan | 60-144224 |
| Jul. 1, 1985 | [JP] | Japan | 60-144225 |

[51] Int. Cl.$^4$ .................................... G01N 21/86
[52] U.S. Cl. ........................... 250/571; 356/444
[58] Field of Search ............ 250/559, 571; 356/443, 356/444; 354/402, 403, 404, 405, 406, 409; 358/287, 294

[56] References Cited

U.S. PATENT DOCUMENTS

| 3,942,898 | 3/1976 | Anderson | 250/559 |
| 3,994,587 | 11/1976 | Yamamoto et al. | 356/444 |
| 4,080,066 | 3/1978 | Betzold et al. | 250/559 |
| 4,210,818 | 7/1980 | Green et al. | 250/559 |
| 4,229,107 | 10/1980 | Childers | 356/443 |
| 4,266,872 | 5/1981 | Mitsuhashi | 356/443 |
| 4,345,831 | 8/1982 | Kachelries | 356/444 |
| 4,464,036 | 8/1984 | Taniguchi et al. | 250/559 |
| 4,568,184 | 2/1986 | Krantz et al. | 356/443 |
| 4,573,798 | 3/1986 | Fujie et al. | 356/444 |
| 4,575,251 | 3/1986 | Hotla et al. | 250/571 |
| 4,674,126 | 6/1987 | Kotera | 382/53 |
| 4,700,237 | 10/1987 | Yoshioka et al. | 358/287 |
| 4,762,985 | 8/1988 | Imai et al. | 250/201 |

Primary Examiner—David C. Nelms
Assistant Examiner—William L. Oen
Attorney, Agent, or Firm—Fitzpatrick, Cella, Harper & Scinto

[57] ABSTRACT

An apparatus for reading a microfilmed image to obtain digital image signal, in which the level of quantizing is determined by measuring the density of image and of background.

90 Claims, 19 Drawing Sheets

Fig. 2A
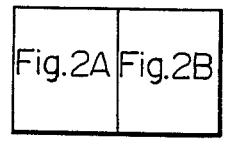
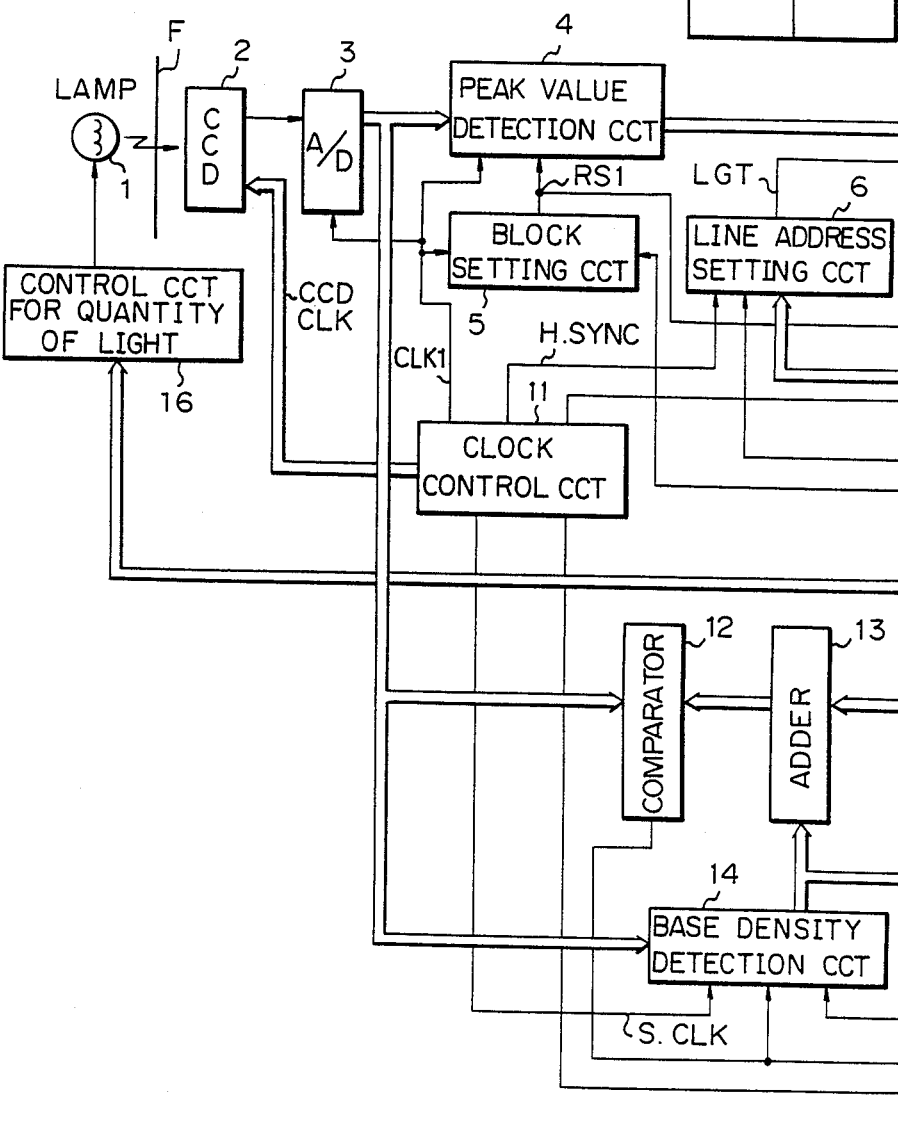

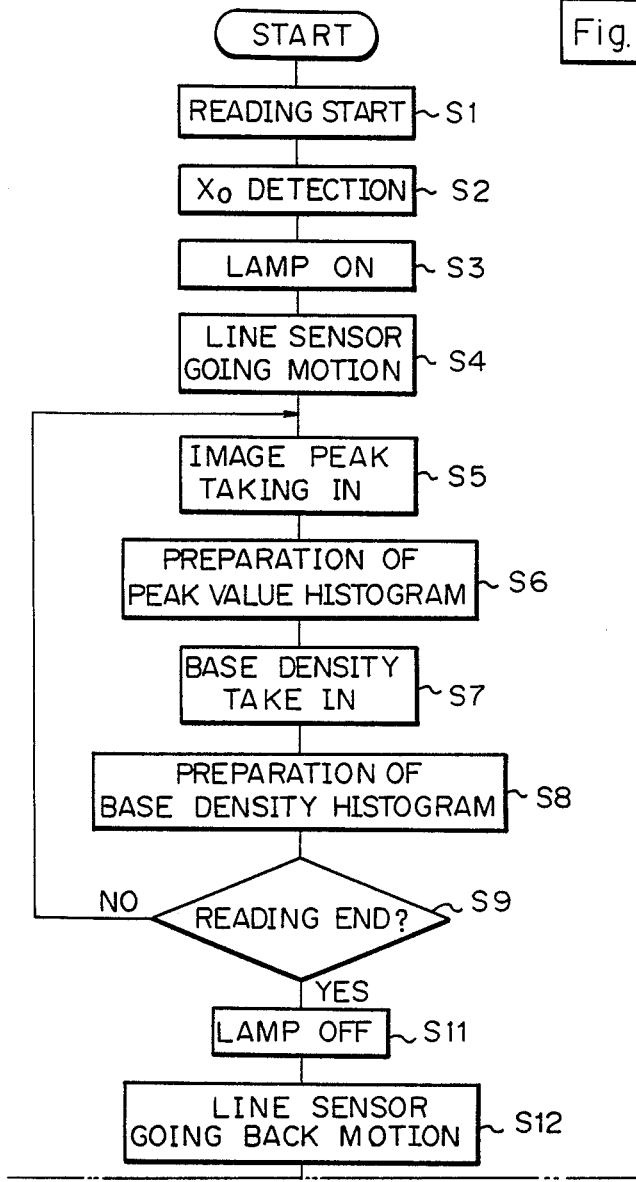

APPARATUS FOR READING A FILM IMAGE WITH CONTROLLABLE ILLUMINATION AND THRESHOLD VALUE

This application is a continuation of application Ser. No. 191,837 filed May 2, 1988, which is a continuation of application Ser. No. 878,790 filed on June 26, 1986, now abandoned.

BACKGROUND OF THE INVENTION

1. Field of the Invention

The present invention relates to an image reading apparatus for illuminating a film bearing an image and reading said image from the light transmitted by the thus illuminated film.

2. Related Background Art

There has already been proposed an apparatus for high-density recording of the information generated in a large quantities, such as of documents, onto microfilms and for reading the recorded image on said microfilms, when required, for reproducing on a recording sheet.

In such apparatus the microfilm is exposed to light, and the density of the light transmitted by the microfilm is detected by an image sensor such as a CCD to obtain an electrical image signal.

For converting the thus obtained image signal for example into a binary signal representing black and white, there is generally conducted a comparison of said image signal with a predetermined threshold value. However the density of image recorded on the microfilm is variable according to the photographing condition, and the use of a fixed threshold value for binary encoding may result in a very dark or faint output image. It is therefore conceived to vary the threshold value according to the density of the recorded image.

Consequently, it is known to photoelectrically detect the amount of light transmitted by the microfilm, in order to determine the threshold value according to the density of recorded image. However, the size and position of the images recorded on the microfilm are not constant, so that, if the threshold value is determined, for example, by the light transmitted by the entire area of film, the exact image density cannot be detected as the transmitted light through a non-image area affects the determination of the threshold value.

On the other hand, it is also conceivable to determine the threshold value from the peak density of the recorded image. However, if characters and symbols of different sizes are present in an image, an image density corresponding to a large character is detected as the peak value, and small characters may be omitted in the reproduced image when binary encoding is conducted with a threshold value determined according to such peak value.

In addition, the background or base density varies according to the type of the microfilm, and the image contrast varies according to such base density even if the image density recorded on the film is constant. Consequently, a threshold value, which is determined solely by the image density recorded on the film, may not be able to achieve exact binary encoding of images close to the background or base density.

Also, the output of the image sensor may fluctuate due to time-dependent change or the circumferential condition of the light source and of the image sensor, thus affecting the determination of an appropriate threshold value.

The output image signal is influenced by the amount of light emitted from the light source for illuminating the microfilm. It is therefor conceivable to control the amount of light at a constant value. However, as explained above, the amount of light transmitted by the microfilm is governed by the base density thereof, which is variable according to the type of film and the developing conditions thereof. Consequently, a constant amount of light alone does not ensure satisfactory image reading from different films.

It is therefore conceivable to detect the amount of light transmitted by the film and to regulate said amount of light to be always to an optimum value regardless of the base density. However, such method of control with the transmitted light is unable to achieve appropriate control in the case that film has a local smear or scar.

Also, in such conventional apparatus, the image reading of microfilm has required an operator for confirming that an image frame on the microfilm is projected in a correct position, through inspection of a projection screen, since otherwise a non-image area between image frames on the film may be erroneously read.

SUMMARY OF THE INVENTION

In consideration of the foregoing, an object of the present invention is to enable satisfactory reading of an image recorded on a microfilm or the like.

Another object of the present invention is to enable, in reading an image recorded on a film such as a microfilm, appropriate determination of a threshold value for digitizing of image signal according to the image density.

Still another object of the present invention is to enable satisfactory reading of an image recorded on a film and containing characters and symbols of different sizes.

Still another object of the present invention is to enable, in reading an image recorded on a film such as microfilm satisfactory image reading by suitably regulating the amount of light to which the film is exposed.

Still another object of the present invention is to provide a film exposing apparatus capable of efficiently and securely an abnormality in a light source for illuminating a film.

Still another object of the present invention is to be exposed of a film is securely exposed in a correct exposing position.

According to the present invention, these objects are attained by provision of a film image reading apparatus having, according to one aspect of the invention, first and second detection means, which are respectively for detecting an image density of an image recording on an illuminated film, on the basis of image signals from a reading means, and for detecting a base density of the film on the basis of the image signals. The image signals are then quantized, using a threshold value determined on the basis of the detected image density and the base density. The image density may be determined using a peak value of the image signals.

According to another aspect of the invention, the image signals for each reading line are divided into plural block, each of which includes a predetermined amount of image signal, and a peak value of each block is detected. The image signals are then quantized using a threshold value determined on the basis of the detected peak value for each block.

According to another aspect of the invention, quantization is performed using a threshold value determined on the basis a detected density of an image corresponding to a predetermined partial area of an illuminated film.

According to still another aspect of the invention, an output value from a reading means is detected while a film bearing an image is not illuminated, and a second detection means detects image density of the image from signals from the reading means, while the film is illuminated. A quantization threshold value is determined on the basis of the thus detected up value and image density.

According to another aspect of the invention, a first detection means detects a base density of a film output during reading of a non-image area of the film illuminated by an illuminating means, the amount of light of the illuminating means is determined according to the detected base density, and a second detection means detects image density of the image based on an output from the reading means during reading of the image illuminated with the thus determined amount of light.

The foregoing and still other objects of the present invention, and the advantages thereof, will become fully apparent from the following detailed description.

DETAILED DESCRIPTION OF THE PREFERRED EMBODIMENTS

Now the present invention will be clarified in detail by reference to the preferred embodiments thereof.

Figure 1:
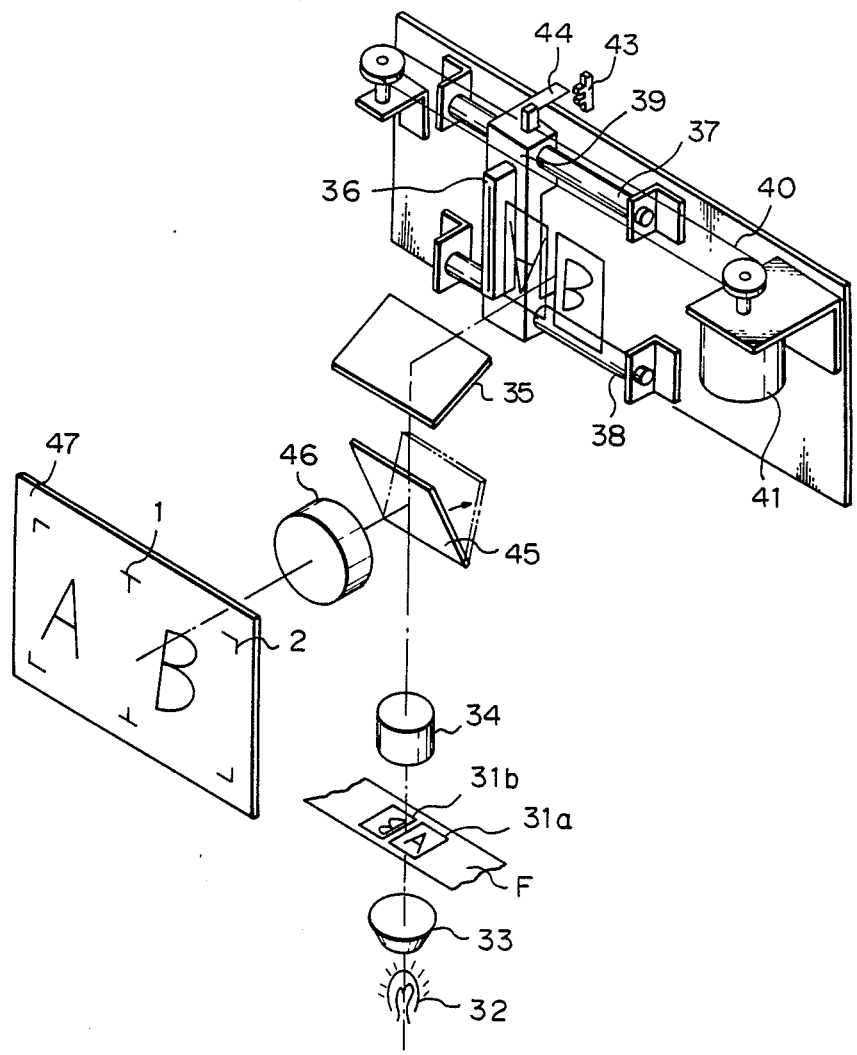
FIG. 1 is a schematic perspective view of a microfilm reading apparatus embodying the present invention.

FIG. 1 is a schematic perspective view of a microfilm reading apparatus embodying the present invention.

In FIG. 1, frames 31a, 31b of a film F is illuminated by light emitted from a halogen lamp 32 and converged by a condenser lens 33. The light transmitted by the images of thus illuminated frames 31a, 31b of the film F is guided through an optical system composed of an imaging lens 34 and a fixed mirror 35 and focused on a linear sensor 36 composed for example of a charged-coupled device (CCD). Said linear sensor 36 is fixed on a reciprocating carriage 39 guided by paired parallel guides 37, 38. The carriage 39, being connected to a wire 40 transmitting the rotation of a motor 41, moves the linear sensor 36 in a sub-scanning direction perpendicular to the main scanning direction thereof, thus reading image information for each line. Image signal obtained by reading the image in this manner is released as binary signal.

In the main body of the apparatus there is provided a photointerruptor 43 for detecting the start of scanning operation, which generates a start timing signal when the light in said photointerruptor 43 is intercepted by a light shield plate 44 fixed on the carriage 39 in the course of movement thereof.

Between the imaging lens 34 and the fixed mirror 35 there is provided a movable mirror 45 for projecting the images of the frames 31a, 31b of the film F in an enlarged state onto a screen 47, constituting display means, through a projection lens 46. On said screen 47 there are printed a reading frame 1 for a half-size image and another reading frame 2 for a full-size image. In case a vertically oblong recording sheet is set in an unrepresented laser beam printer for image formation on said recording sheet in response to the image signal, said printer prints the half-size area indicated by the frame 1. On the other hand, in case the recording sheet is laterally oblong, the printer prints the full-size area indicated by the frame 2.

Figure 2B:
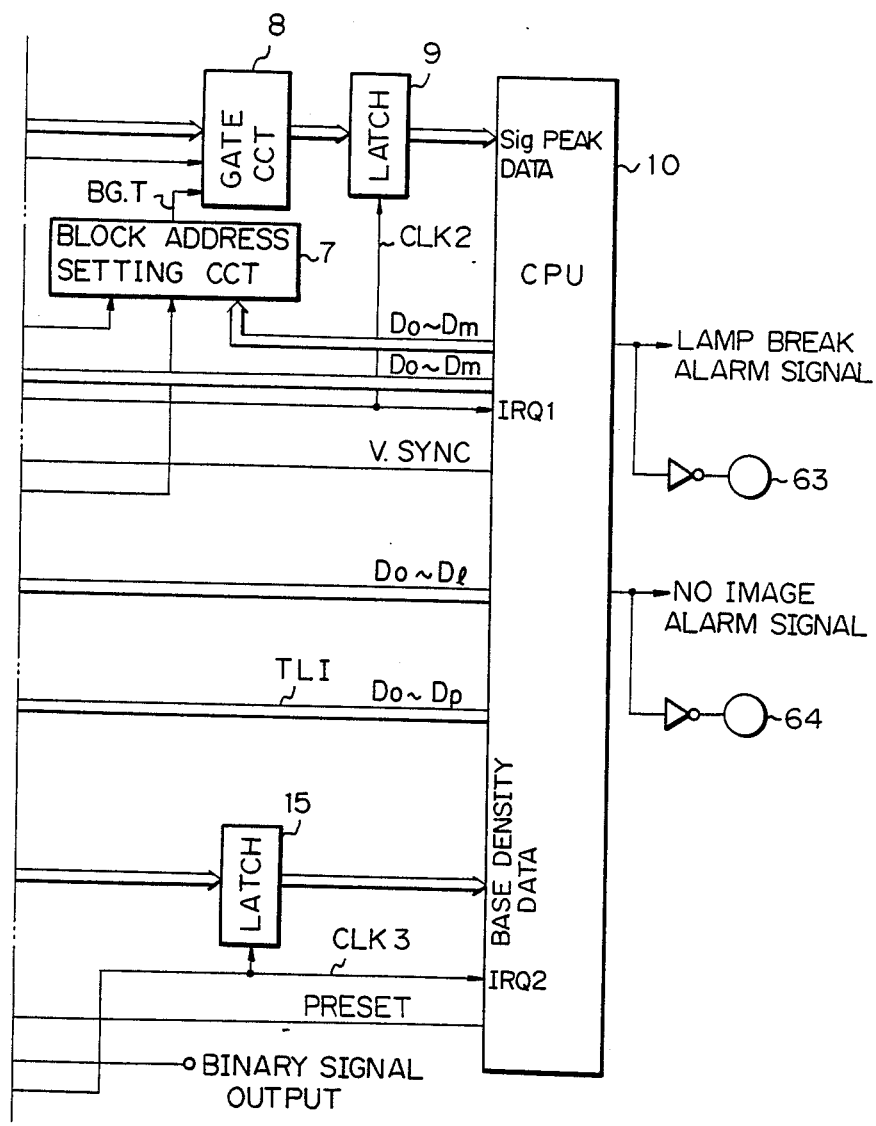
FIG. 2, consisting of FIGS. 2A and 2B, is a block diagram showing an example of a circuit for processing an image signal.

FIG. 2, consisting of FIGS. 2A and 2B, is a block diagram of a circuit for determining a threshold value for binary encoding the analog image signal from the linear sensor.

In the present embodiment, the image placed at the reading position of the reading apparatus is read twice. In the first reading, the threshold value for binary encoding of the image signal is determined according to the data obtained from the linear sensor, and, in the second reading, the image information released from the linear sensor is binary encoded according to the threshold value determined in the first reading.

In FIG. 2, a lamp 1 illuminates a microfilm F. A linear image sensor 2, composed for example of a CCD, reads the image of the microfilm, by the light transmitted through the microfilm F. The current of the lamp 1 is controlled by a light quantity control circuit 16 according to the base density of the film to be read, thereby enabling the linear sensor 2 to read the image in optimum state.

An analog-to-digital (A/D) converter 3 converts the analog image signal from the linear sensor 2 into a digital signal, containing N bits for representing density of each pixel.

A peak value detection circuit 4 detects the peak value of the light level of the serially entered image signal. Said peak value detection circuit 4 divides the image signal of a scanning line into plural blocks and detects the peak value of the image signal in each block. The image signal obtained in one scanning operation is divided into blocks each containing a predetermined number of pixels, by means of a block setting circuit 5.

The block setting circuit 5, for dividing a scanning line into a certain number of blocks, is a frequency dividing circuit composed of an N-bit counter of which counting operation is triggered by a horizontal synchronization signal HSYNC synchronized with each scanning operation of the linear sensor 2. According to the selection of N bits for a unit block, the scanning line is divided into an arbitrary number of blocks of N bits each.

Figure 6:
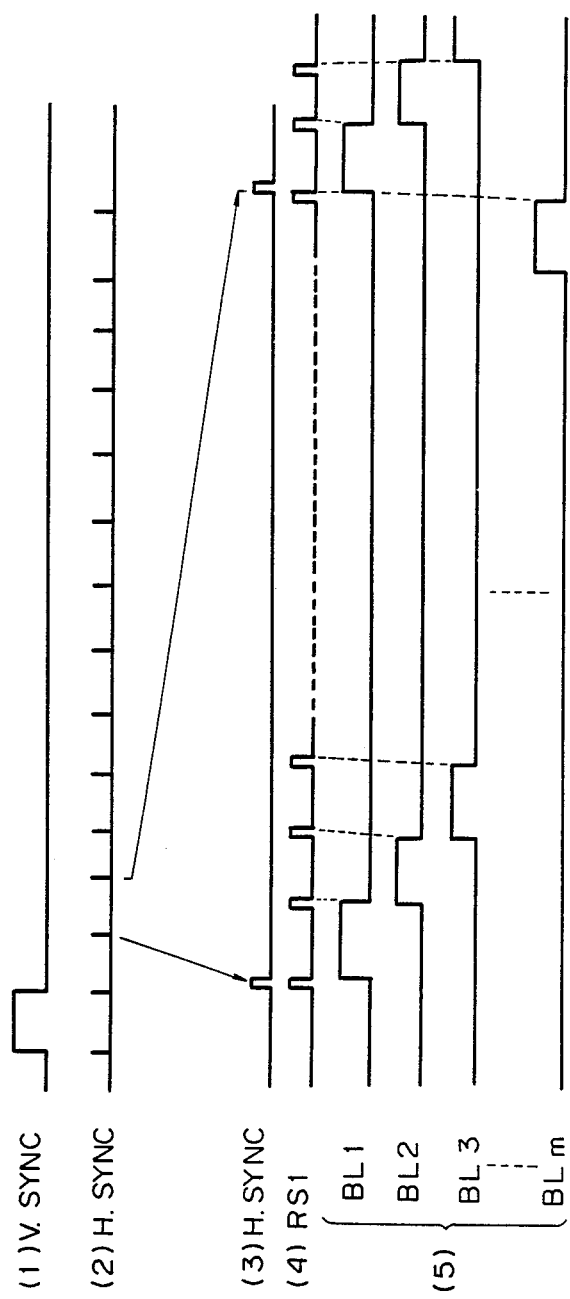
FIG. 6 is a chart showing a scanning line dividing operation.

FIG. 6 shows the dividing operation of division of a scanning line by said block setting circuit 5. In FIG. 6, a chart (1) shows a vertical synchronization signal VSYNC synchronized with the start of reading of an image by the linear sensor 2. A chart (2) shows the horizontal synchronization signal HSYNC synchronized with each main scanning operation of the linear sensor 2. The block setting circuit 5, composed of a frequency dividing circuit of an N-bit counter, is cleared by the horizontal synchronization signal HSYNC, counts the clock signal CLK1 from a clock control circuit 11 and supplies a reset signal RSl at every N count to the peak value detection circuit 4 as shown in a chart (4). Therefore, as shown in a chart (5), a main scanning period between two horizontal synchronization signals HSYNC is divided into m blocks BL1-BLm. The number m of divisions is suitable selected in consideration of the size of characters and symbols in the image recorded on the microfilm.

The peak value detection circuit 4 always detects the peak value of each block, since the output signal of the block setting circuit 5 is used as a reset signal RSI for said peak value detection circuit 4 as explained above.

A line address setting circuit 6 counts the horizontal synchronization signal HSYNC synchronized with each main scanning operation of the linear sensor 2 and sets an address area in the sub-scanning direction according to the count.

Figure 3:
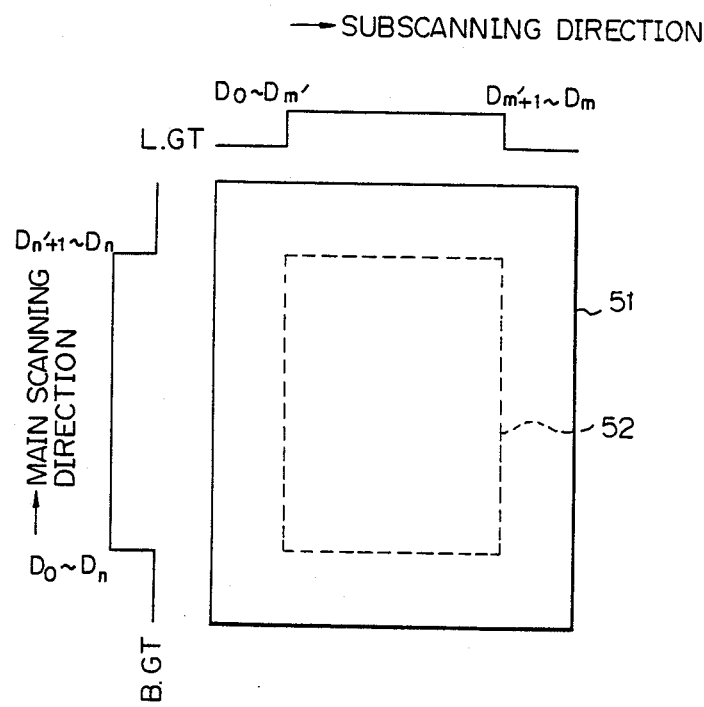
FIG. 3 is a view showing a threshold determining area.

A block address setting circuit 7 sets a block area under scanning. A CPU 10 presets data D0–Dn of n+1 bits and data D0–Dm of m+1 bits to the line address setting circuit 6 and the block address setting circuit 7, thus setting an image area, or a threshold determining area, as shown in FIG. 3, for determining the threshold value for binary encoding the image signal. In FIG. 3, 51 indicates the entire reading area of the linear sensor, while 52 indicates the threshold determining area. In this manner, for determining the threshold value, there is defined an area smaller than the entire reading area, and the peak value obtained in said smaller area is considered as the peak value effective for determining the threshold value. Thus, in consideration of the variation in the image size or image position on the film, the peak value obtained in film portions other than the image is disregarded. Said smaller area is naturally selected at a position and with a size such as always to contain the image.

Figure 4:
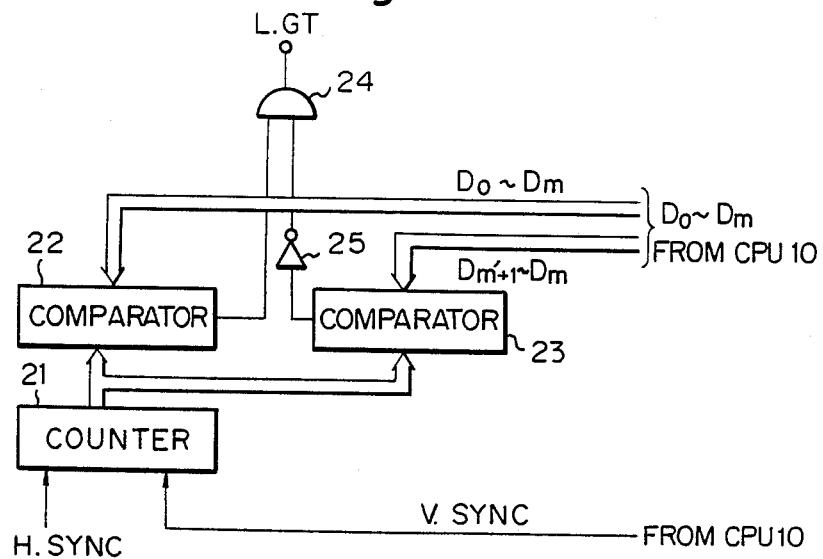
FIG. 4 is a block diagram of a line address setting circuit.

FIG. 4 shows an embodiment of the line address setting circuit 6, which is composed of a counter 21, two comparators 22, 23, an AND gate 24 and an inverter 25. The counter 21 is triggered by the vertical synchronization signal VSYNC indicating the start of scanning of an image and counts the horizontal synchronization signal HSYNC. The count output signal of said counter 21 is compared in the comparator 22 with addresses D0-Dm' released by the CPU 10 and indicating the area start point in the sub-scanning direction, and also is compared in the comparator 23 with addresses Dm'+1 - Dm indicating the area end point. Each counter releases a signal "1" when the count coincides with each of said addresses. The output of the comparator 22 and the inverted output of the comparator 23 are guided to the AND gate 24 to obtain a line gate signal L-GT which assumes the high-level state "1" from the start point to the end point of the area.

In this manner the area can be defined by said line gate signal in the sub-scanning direction.

Figure 5:
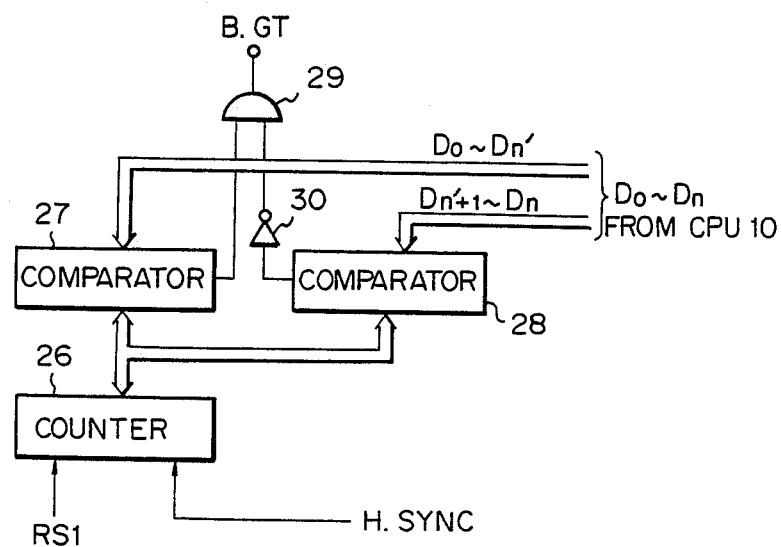
FIG. 5 is a block diagram of a block address setting circuit.

FIG. 5 shows an embodiment of the block address setting circuit 7 which is composed of a counter 26, two comparators 27, 28, an AND gate 29 and an inverter 30. The counter 26 is triggered by the horizontal synchronization signal HSYNC and counts the signal RSl supplied from the block setting circuit 5. The count released from said counter is compared in the comparator 27 with starting addresses D0–Dn' of the block areas in the main scanning direction released from the CPU 10, and is also compared in the comparator 28 with end addresses Dn'+1-Dn of the block areas. Each of the comparators releases a signal "1" when the count coincides with the address. The output signal of the comparator 27 and the inverted output signal of the comparator 28 are guided to the AND gate 29 to obtain a block area signal B-GT which assumes a high-level state "1" from the start point to the end point of the area.

In this manner the area can be defined by said block area signal in the main scanning direction.

In FIG. 2B there is shown a gate circuit 8 which defines a two-dimensional area 52 as shown in FIG. 3 from the block area determined by the block address setting circuit 7 and the line area determined by the line address setting circuit 6, and transmits the peak values in the area 52 only, from among the peak values detected by the peak value detection circuit 4.

Figure 7:
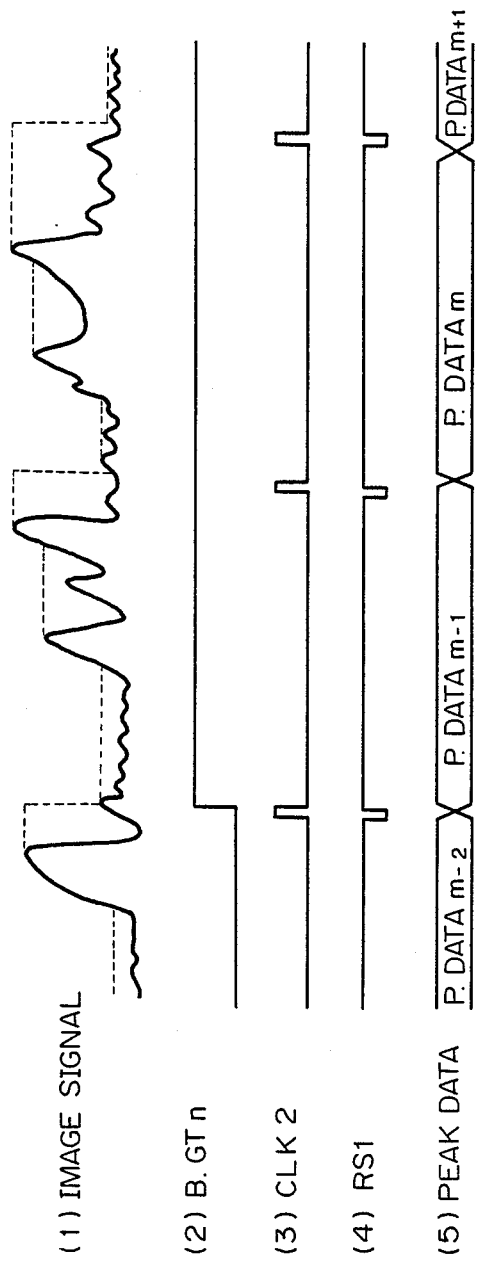
FIG. 7 is a chart showing a peak value fetching operation.

FIG. 7 shows the peak value fetching operation by the block area signal B-GT. In FIG. 7 there are shown image signal (1), block area signal (2), clock signal CLK2 (3) for determining the latch timing of a latch circuit 9 to be explained later, reset signal RSl (4) and peak data (5). When the count of the reset signal RSl reaches the data D0–Dn' indicating the start point of the threshold determining area, the block address setting circuit 7 shifts the block area signal B-GT to high-level state, whereby the gate circuit 8 renders effective the peak value detected by the peak value detection circuit 4.

Said threshold determining area is suitably determined in consideration of the position and size of the image on the microfilm.

As explained above, the line address setting circuit 6 and the block address setting circuit 7 respectively release high-level signals over ranges defined by the CPU 10. Thus a period in which said two signals are both at the high-level state corresponds to the peak value fetching area 52 shown by broken lines in FIG. 3, and the peak value entering the gate circuit 8 during said period is considered effective.

The peak value fetching area is limited as explained above, because the size and position of the image on the microfilm are not fixed, so that the peak value obtained over the entire reading area of the linear image sensor 2 may not represent the exact peak value of the image but may represent a non-image density such as the background or base density. Therefore, a predetermined area, in which the image should always be present, is defined inside the reading area of the image sensor 2 and the peak values obtained inside said predetermined area alone are considered effective. In this manner it is rendered possible to securely obtain the peak value of the image.

A latch circuit 9 is provided for determining the time of fetching the peak value by the CPU according to the signal CLK2. The microcomputer unit (CPU) 10 for controlling the function of the apparatus fetches the latch data of the latches 9, 15 in respective synchronization with the clock signals CLK2, CLK3. A clock control circuit 11 generates various timing clock signals used as the standards of function of the apparatus.

A comparator 12 generates a binary image signal through comparison of the analog image signal with the threshold value formed according to a predetermined procedure.

An adder 13 adds the output of a base density detection circuit 14 to be explained later to threshold value information TL1(DO-Dp) from the CPU 10 and supplies the threshold value to the comparator 13.

Figure 8:
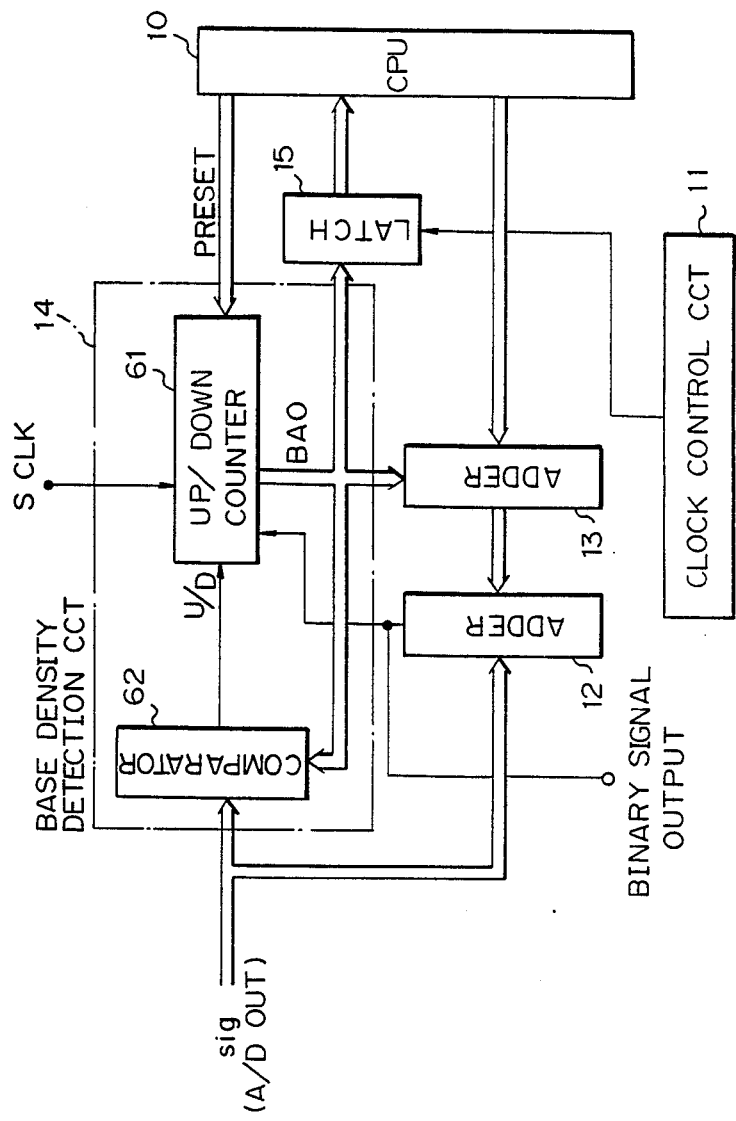
FIG. 8 is a block diagram of a base density detecting circuit.

FIG. 8 shows an embodiment of the base density detecting circuit 14, composed of an up-down counter 61 and a comparator 62. The output BAO of the up-down counter 61 is compared with the digital image signal SIG from the A/D converter 3 to increase or decrease a value PRISET predetermined by the CPU 10. More specifically, the count of the up-down counter 61 is decreased or increased respectively when BAO is larger or smaller than the signal SIG.

Figure 9:
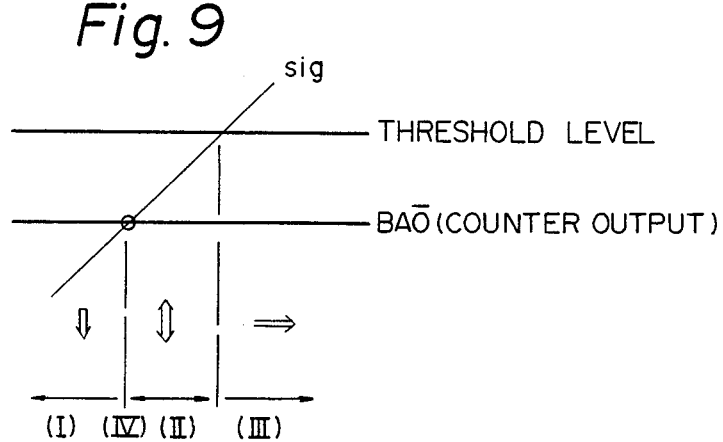
FIG. 9 is a chart showing the function of said base density detecting circuit.

This operation will be more specifically explained in FIG. 9 which illustrates the relationship among the counter output BAO, threshold level and A/D output signal SIG. In an area (I) where BAO>SIG, the up-down counter 61 reduces the count. In an area (II) where threshold level≧SIG>BAO, said counter 61 increases the count. In areas (III) and (IV) the up-down counter 61 suspends the counting operation and retains the previous count.

In this manner a value close to the minimum level of the digital image signal SIG can be determined and said value BAO is regarded as an approximate background or base density. The sampling clock signal CLK3 determines the timing of fetching the approximate base density into the CPU 10 and can be arbitrarily selected. A latch circuit 15 is provided for fetching the approximate base density into the CPU 10 in response to the sampling clock CLK3.

The light quantity control circuit 16 controls the current to the lamp 1 for regulating the amount of light thereof, in response to an instruction DO-Dl of the CPU 10. An indicator 63 is provided to indicate a lamp failure. Also an indicator 64 is provided to indicate that the image to be read is not in a normal reading position.

Figure 14B:
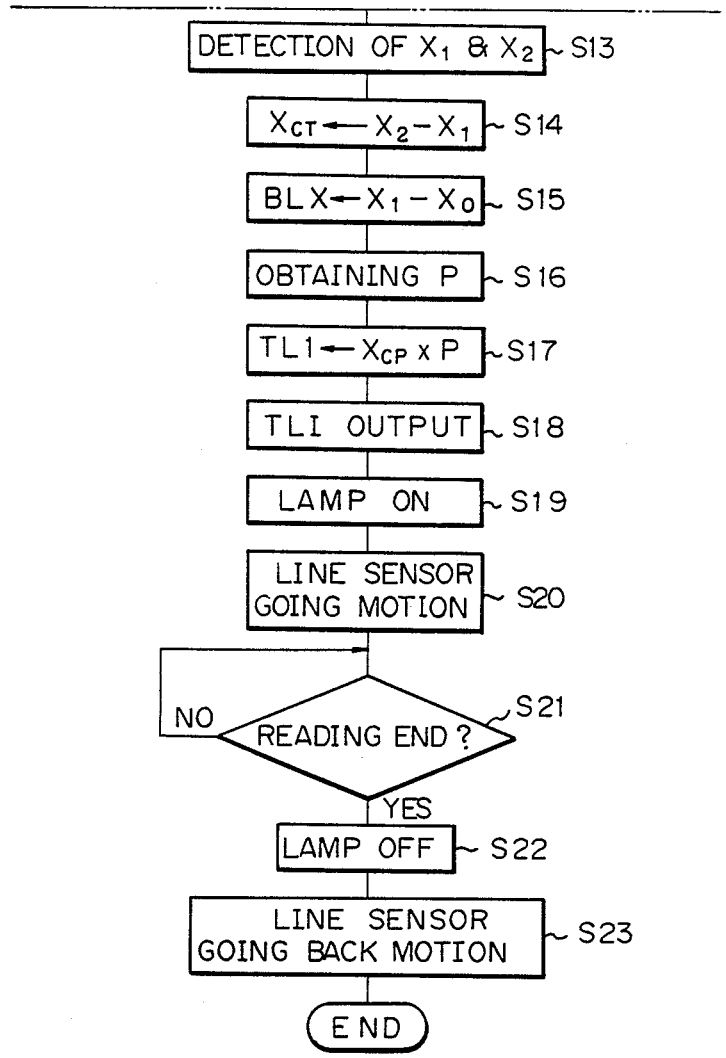
FIG. 14, which consists of FIGS. 14A and 14B is a flow chart showing the procedure of determining the threshold value.

In the following there will be explained the function of the above-described circuit, while making reference to a flow chart of the control procedure of the CPU 10 as shown in FIG. 14. A program corresponding to said flow chart is stored in advance in a ROM incorporated in the CPU 10.

When an image frame to be read of the microfilm is set in a predetermined reading position to enable reading operation, the CPU 10 fetches data X0 as a reference signal for the base density. More specifically, the linear sensor effects a reading operation in the absence of light (step S1) and the corresponding output X0 is fetched (step S2). Thereafter the lamp 1 is turned on to start the first image reading for determining the threshold value for binary encoding of the image data (step S3), and the linear sensor 2 initiates forward movement (step S4).

Figure 10:
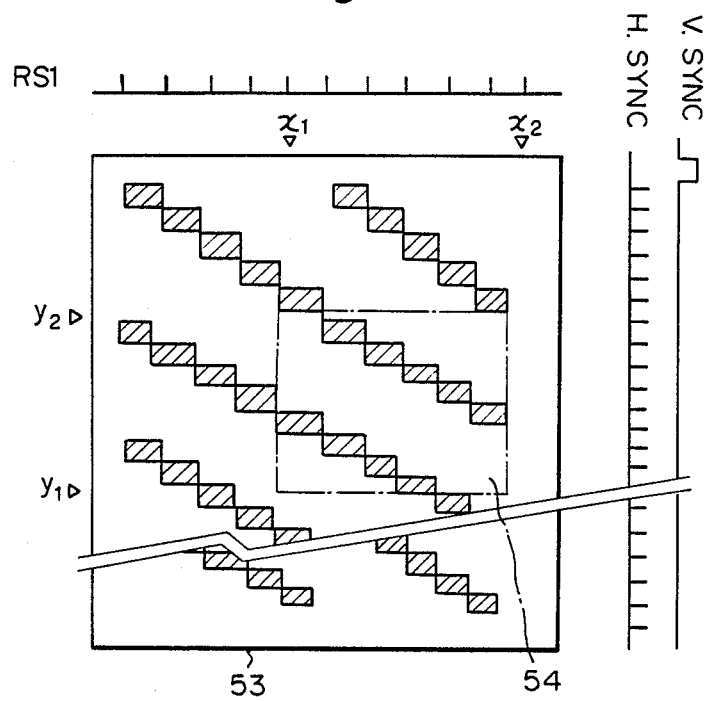
FIG. 10 is a view showing the mode of data fetching from the threshold determining area.

Then the peak value of the digital image signal SIG and the approximate base density are fetched in the threshold determining area defined in advance as explained before (steps S5, S7). More specifically, as shown in FIG. 10, the start and end points of said area are set by xl(DO-Dm') and x2(Dm'+1-Dm) in the main scanning direction, and those in the sub-scanning direction are set by y2(DO-Dn') and yl(Dn'30 1-Dn). In this manner the data in a chain-lined frame 54, instead of the full-lined entire reading area 53, are fetched for determining the threshold value.

Figure 11:
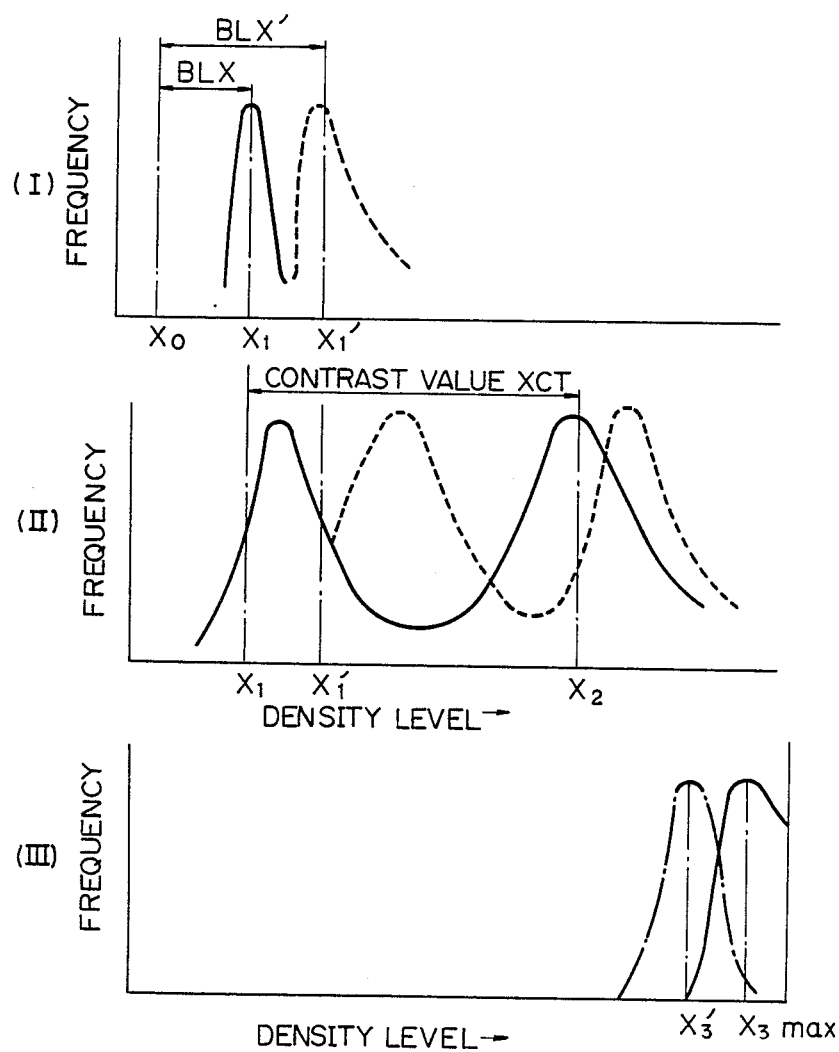
FIGS. 11 (I), (II), and (III) are charts showing examples of histograms.

After the completion of the first image reading (step S9), the lamp 1 is turned off and the linear sensor 2 is returned (step S12). Then the CPU 10 prepares, for determining the threshold value for binary encoding of the image signal, a histogram showing frequency in Y-axis against density level in X-axis as shown in FIG. 11 from thus fetched data (steps S6, S8). In FIG. 11 there are shown two histograms in full line and broken line, corresponding to two different films.

FIG. 11 (I) is a histogram of the approximate base density, obtained by sampling the lowest level area of the image signal with the background density detection circuit 14.

FIG. 11 (II) shows the peak value data of the image signal in the above-mentioned threshold determining area, obtained, in case of a negative film, by sampling the area of highest light transmission.

If the peak value is determined for each scanning line, and if the image contains large characters of low spatial frequencies and small characters of high spatial frequencies, the peak value will be sampled from such large characters, so that the small characters may not be reproduced or may be reproduced unsatisfactorily. However, it is rendered possible to obtain peak values corresponding to large and small characters even if they are mixedly present, by dividing the scanning line into plural blocks and sampling the peak value in each block.

The curve shown in FIG. 11 (II) shows two peaks, the one at the lower density representing the base density while the other at the higher density representing the peak in the image signal. Thus a density level x2 corresponds to the highest frequency of the image signal peaks in the threshold determining area in a film of a first base density.

In the curve shown in FIG. 11 (I), Xl represents a value close to the base density of the film of the first base density (called approximate base density) and corresponds to the highest frequency of the data obtained by the background density detection circuit 14. X1' is a similar density obtained for a film with a second base density which is lower than said first base density. In general, the base density of a film fluctuates according to the developing conditions and varies according to the specy of film. Also, in the chart shown in FIG. 11 (II), the broken-lined second base density is lower than the solid-lined first base density.

In such a solid-lined histogram, there are detected a value X1 representing the approximate base density and a value X2 representing the peak density of the image signal (step S13), and the contrast XCT is determined as the difference $X2-X1$ of said two values (step S14). Said contrast XCT is not necessarily the same for characters of the same given spatial frequency, as it is dependent on the film processing in the same manner as is the base density. Consequently, the same density cannot be obtained on the copy by merely employing, as the threshold value for binary encoding of the image signal, a half of said contrast value XCT. In the present embodiment, therefore, a correction is applied to the contrast $XCT=X2-X1$ according to the base density in order to obtain a uniform or consistent density on the copy.

Figure 12:
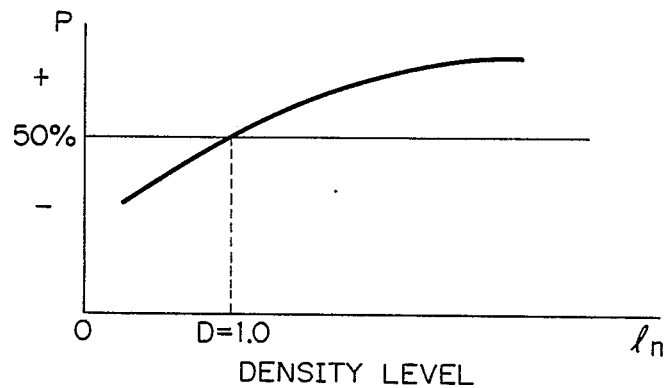
FIG. 12 is a chart showing the relation between the base density and correction coefficient.

FIG. 12 shows a calibration curve employed for this correction, representing a coefficient to be multiplied on the contrast XCT in the ordinate, as a function of the base density in the abscissa. The original point corresponds to a totally black film with no transmittance, and the film base density decreases along the x-axis. At a point $D=1.0$ on the x-axis corresponding to a base density of $D=1.0$, the threshold value becomes equal to a half (50%) of the contrast XCT.

Figure 13:
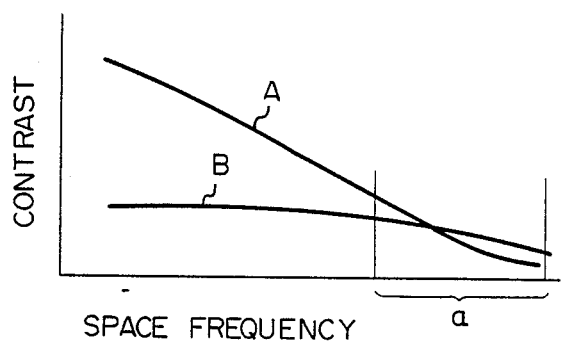
FIG. 13 is a chart showing the relation between the spatial frequency and contrast.

FIG. 13 show the relation between the contrast in the ordinate and the spatial frequency in the abscissa, with the base density as a varying parameter.

A curve (A) shows the behavior of a film with a high base density, while a curve (B) shows that of a film with a low base density In general the usual characters in the newspaper belong to a spatial frequency as shown in FIG. 13, and, in said range a, the contrast is lower as the base density is higher. Consequently the same density on the copy is obtained regardless of the base density, by taking a point $D=1.0$ on the calibration curve shown in FIG. 12 as a reference and decreasing or increasing the correction coefficient P to be multiplied on the contrast respectively when the base density is higher or lower than the reference value.

However, the approximate base density X1 of the highest frequency shown in FIG. 11 is in fact not constant even for a particular species of film, because of fluctuation in the amount of light, in the film product and in the temperature of the electric circuit. In order to compensate such fluctuations, therefore there is employed the aforementioned $x_)$ (FIG. 11 (I)).

As already explained, the value $x_O$ is obtained as the output of the linear sensor 2 in the absence of light. Said value is read at a regular interval for preparing a histogram, and in this manner it is rendered possible to process the sampled data with a high precision, absorbing fluctuations resulting from the product quality, electric circuit, temperature etc.

In FIG. 11 (I), a value $BLX=X_1-x_0$ is obtained by subtracting the correction value $x_0$ from the approximate base density $X_1$ (step S15). Said value BLX is a correction base density of a film of a first base density, while another value $BLX'=X'_1-X_0$, obtained by subtracting the correction value x from the approximate base density $X'_1$, is the correction base density of a film of a lower second base density. Correction coefficient P is obtained from the calibration curve shown in FIG. 12, corresponding to said correction base density BLX or BLX' (step S16) and is multiplied on the contrast XCT (step S17). The result of said multiplication can be used as the threshold information TLI useful for determining the appropriate threshold value for binary encoding for films of different base densities.

Based on a histogram thus prepared, the CPU 10 executes the above-explained process, and supplies the adder 13 with threshold value information TLI constituting a reference for the threshold value for binary encoding the image signal (step S18).

The adder 13 adds the base density from the background density detection circuit 14 to said threshold information TLI to obtain a threshold value for supply to the comparator 12 as explained before. In this manner the threshold value is obtained in consideration of the image recorded on the film and the base density thereof, and is used for binary encoding, in the comparator 12, the digital image signal obtained from the A/D converter 3 in the second image reading.

More specifically, the lamp 1 is again turned on (S19), and the linear sensor 2 is driven in the forward direction (step S20) to effect image reading. The analog image signal from the linear sensor 2 is converted by the A/D converter 3 into a digital image signal which is compared in the comparator 12 with the threshold value, obtained by adding the base density to the threshold information TLI from the CPU 10, thus being binary encoded.

Upon completion of the image reading (step S21), the lamp 1 is turned off (step S22) and the linear sensor 2 is returned to the start position (step S 23). In this manner the image reading is completed.

FIG. 11 (III) shows dynamic transmittance of a film base. A point X corresponds to the maximum frequency of a histogram of the output of the linear sensor 2 when the lamp 1 is turned on but the film is not inserted in the film reading position. When the film is inserted into said reading position, the amount of light decreases to a level X ' by the absorption of the film base, so that the relative resolving power of the image signal is reduced. Thus is inserted in said reading position, and a reading operation is conducted, by moving the linear sensor, in a non-image area, such as a leader portion of the film. In this operation the amount of light is so regulated as to reach a light quantity level of $X_3$, thereby maximizing the resolving power of the image signal.

It is thus rendered possible to compensate the loss in light quantity resulting for example from a local stain on the film or a fluctuation in the amount of light from the lamp, as the data for light quantity regulation are sampled not from a single point of the film but from the light transmitted through a predetermined area. Also it is possible to obtain a satisfactory copy density even from a low contrast image for which the relative resolving power for the signal is lowered, by increasing the amount of light and effecting binary encoding at a necessary contrast.

Figure 15A:
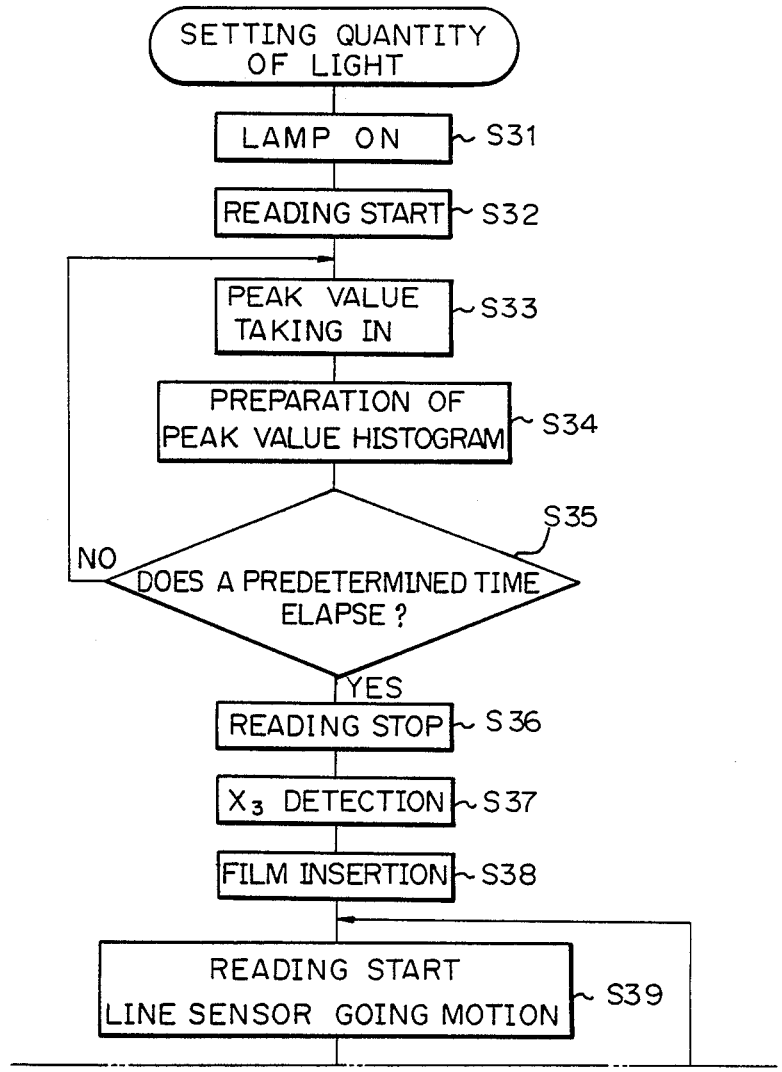
FIG. 15, which consists of FIGS. 15A and 15B, is a flow chart showing the procedure of determining the amount of light.
Figure 15B:
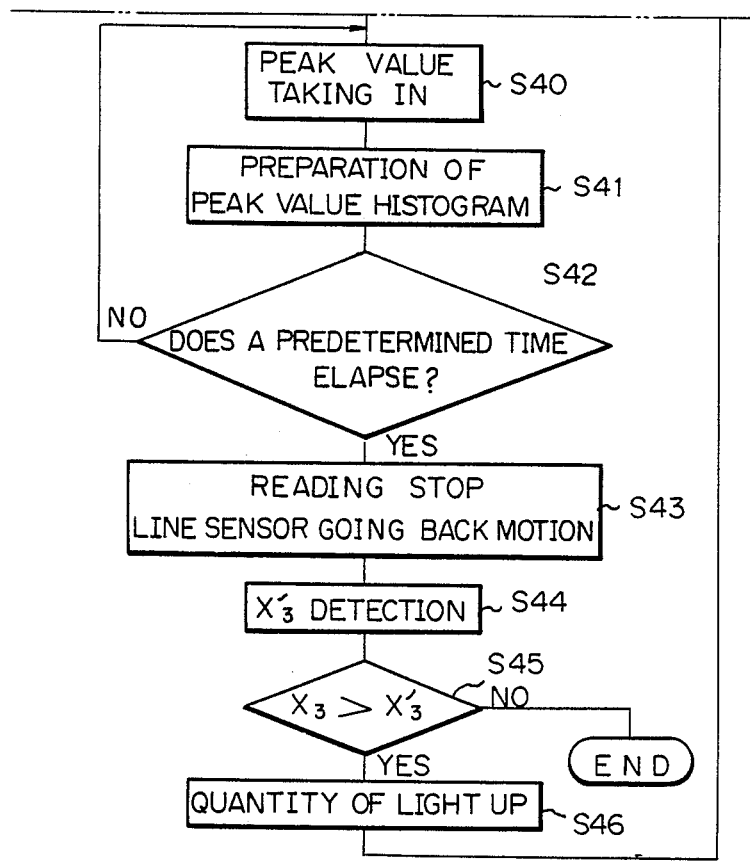

FIG. 15 shows the procedure for light quantity setting utilizing a histogram. A corresponding program is also stored in a read-only memory incorporated in the CPU 10. This light quantity setting operation is executed for example before the image reading operation shown in FIG. 14.

At first, in a state in which the film is not in the reading position, for example the film is not loaded or rewound if already loaded, the lamp 1 is turned on with a reference amount of light (step S31). Then the linear sensor 2 is started to initiate the image reading (step S32), a peak in the output of the linear sensor 2 is determined (step S33), and a histogram of the peak values is prepared (step S34). When the reading operation is completed after a predetermined period (step S35), the reading operation is terminated (step S36), and the value $X_3$ (III In FIG. 11) is detected from thus prepared histogram (step S37).

Then the film is loaded, and a non-image area thereof is set in the reading position (step S38). Then the linear sensor is activated again to start the reading operation, and is put into forward motion (step S39). The peak value of the output of the linear sensor 2 in this operation is fetched (step S40), and a histogram of the peak values is prepared (step S41). After the completion of the reading operation for a predetermined period (step S42), the reading operation is terminated and the linear sensor is returned (step S43). Then the value $X_3'$ (III in FIG. 11) is detected from the thus prepared histogram (step S44).

Then said values $X_3$ and $X_3'$ thus detected are compared (step S45), and, if $X_3 > X_3'$, the lamp quantity control circuit 16 is so controlled as to increase the amount of light of the lamp by predetermined amount (step S46). Then the linear sensor 2 is driven to effect a reading operation with thus increased amount of light (step S39), then the corresponding peak value is detected (step S40), and a histogram is prepared (step S41). After the reading operation for a predetermined period (step S42), the reading operation is terminated (step S43), then the value $X_3'0$ is again detected from the histogram (step S44), and the values $X_3$ and $X_3'$ are compared (step S46). This operation is repeated until a condition $X_3 \leq X_3'$ is reached, and the amount of light when said condition reached is stored. This amount of light enables image reading with a high resolving power as explained before, and the image on the film is read with said amount of light. The detection of the transmission through the film may be effected by moving the film, instead of moving the linear sensor.

As explained in the foregoing, in reading an image recorded on a microfilm, there can be constantly obtained a satisfactory binary image signal regardless of the species of film or the condition of photographing or developing, since the threshold value for binary encoding the image signal is determined in response to the density of the image to be read and to the base density.

Also, the threshold value is affected only by the image since a sampling area for image density is defined for determining the threshold value and the data obtained from a non-image area are disregarded.

In addition, satisfactory threshold values can be obtained even for an image containing characters and symbols of different sizes, since the samples of image density are obtained in each of plural blocks formed by dividing a scanning line.

Furthermore, the film is always appropriately illuminated regardless of the species of the film as control is made on the amount of light transmitted by the microfilm to be read.

Though the foregoing explanation has been limited to the image reading on a microfilm, the present invention is applicable also to the reading of a 35 mm film or an X-ray film. Also the obtained image signal need not necessarily be binary encoded but can also be converted into digital signal of multi-level with plural threshold values, and such plural threshold values can be determined in a similar manner as the above-explained determination of the threshold value for binary encoding. Also, the image reading may be conducted with a two-dimensional image sensor instead of the linear sensor.

Said threshold determination may be conducted for each image frame of the microfilm, or, in case of consecutively reading plural frames on a single microfilm, conducted for the first frame, in which case the remaining frames may be read with the threshold value thus determined.

As explained in the foregoing, it is rendered possible to determine a threshold value without the influence for example of a non-image area and thus to achieve appropriate digitizing exactly corresponding to the image density, since said threshold value for digitizing the image information is determined according to the image density of a predetermined area of the film to be read.

It is also rendered possible to digitize an image containing characters and symbols of different sizes, since the threshold value for digitizing the image information is determined according to the peak value of image density in each of plural blocks obtained by dividing each image scanning line.

Furthermore it is rendered possible to achieve appropriate digitizing regardless of the species of film or developing condition thereof, since the threshold value for digitizing is determined according to the density of image to be read and the base density of the film.

Furthermore, it is rendered possible to avoid the influence of time-dependent change of the apparatus or of circumferential conditions on the digitizing of image signal, since the threshold value for digitizing the image information is corrected by an image reading output obtained in a state where the film is not illuminated.

Furthermore, it is rendered possible to determine an amount of light suitable for the film without the influence of local smearing or scarring on the film, since the amount of light is controlled according to the result of detection of light transmitted over a predetermined width in a non-image area of the film.

Figure 16:
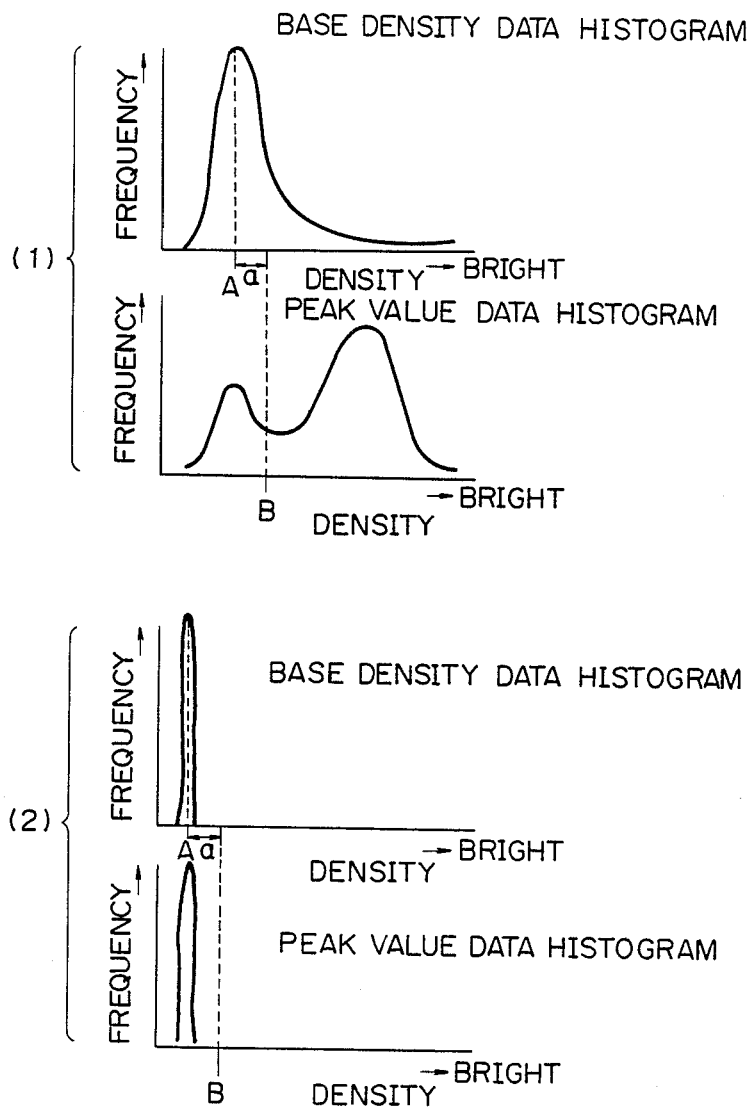
FIG. 16 is a charts showing examples of histograms relating to detection of a lamp failure.
Figure 17:
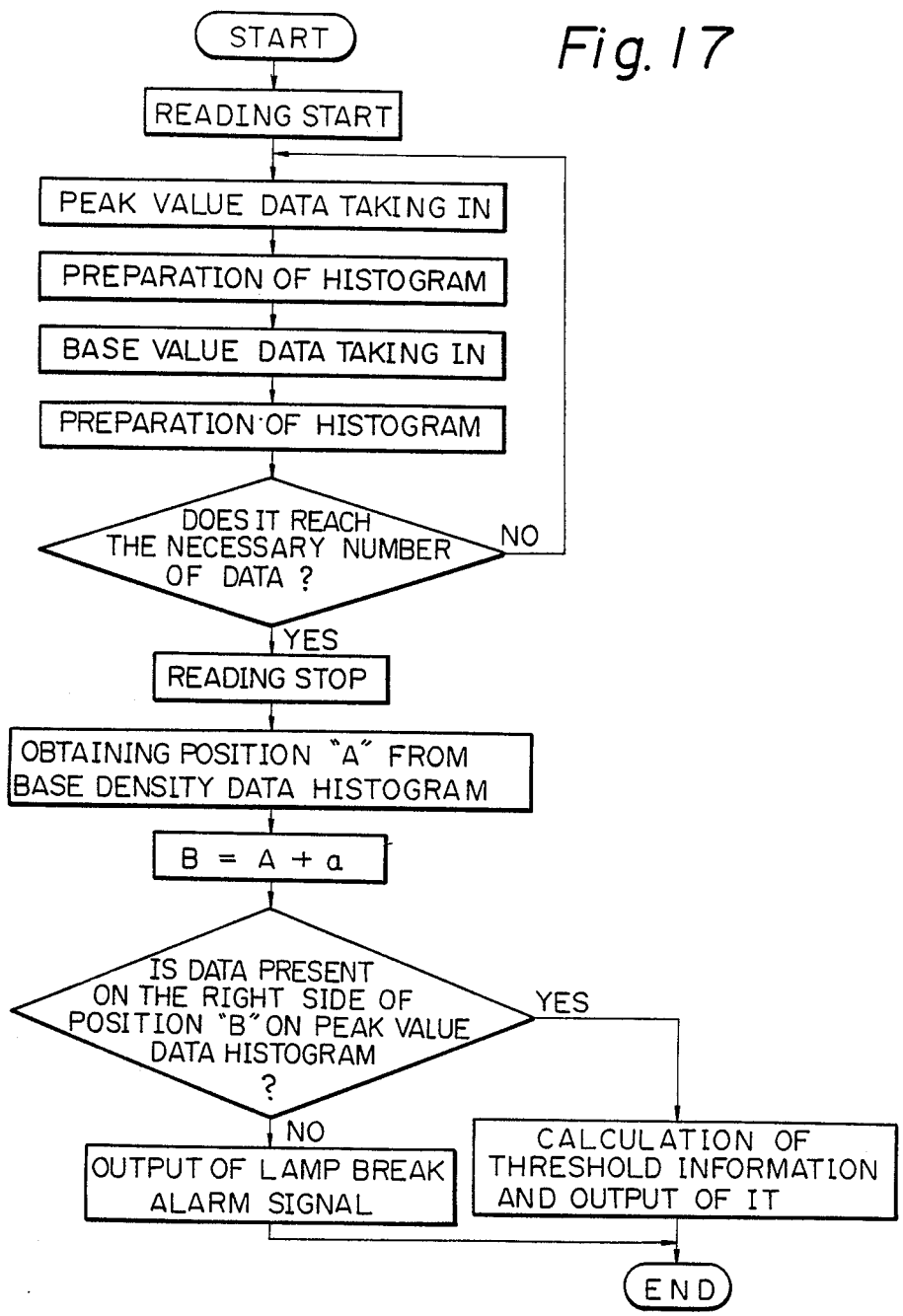
FIG. 17 is a flow chart showing the procedure of detecting a lamp failure.

In the following there will be explained a method of detecting lamp failure in the circuit shown in FIG. 2. FIG. 17 shows a flow chart for this operation, which is programmed in advance in the CPU 10. At first the linear sensor starts a reading operation for peak value detection, and the CPU 10 prepares a histogram by fetching plural data of base density and peak values. In FIG. 16, charts (1) and (2) show histograms in a normal state and in a lamp failure state, in case of a negative film reading. As will be apparent from these charts, the histograms of base density data and of peak value data in the normal state (1) show a wide spreading of data, and the histogram of the peak value data show data in lighter level than the peak position of the histogram of the base density. On the other hand, in case of a lamp failure (2), the peaks of both histograms are positioned at a darkest level A.

Thus the CPU 10 at first locates the peak A in the histogram of the base density data, and, in consideration of statistical error, discriminates whether data are present in the histogram of the peak value data to the right of a position B lighter by a distance a than said peak position A, i.e. at the lighter side of the peak of the base density. If data are absent to the right of the point B, the CPU 10 identifies a lamp failure and releases a lamp failure alarm signal, which is displayed on a display device 63 on the operation panel of the film reading apparatus, in order to a warning to the operator. Said alarm signal may also be utilized for interrupting the image reading operation or printing operation, or may be supplied to a host computer if the microfilm reading apparatus is utilized as an on-line terminal.

On the other hand, in the present of data to the right of the point B, there is identified absence of lamp failure, and density information is released for determining the threshold value from the histograms of the peak values and base density as explained before.

As explained in the foregoing, the lamp failure is detected also from the data distribution of the histograms prepared for determining the threshold value for binary encoding the image signal.

The aforementioned width a for detecting the presence of peak data is regulated in consideration of statistical error and eventual fluctuation in the amount of light from the lamp. Although the foregoing embodiment is limited to the detection of a lamp failure, the present invention is applicable also to the detection of a deficiency in the amount of light from the lamp.

Though the foregoing explanation has been limited to the case of reading a negative film, but, also in case of reading a positive film, the histogram in a normal state shows spreading of data over a wide range while that in an abnormal state such as a lamp failure is concentrated to a dark level. Consequently the abnormality can be detected in a similar procedure.

As explained in the foregoing, it is rendered possible, in a microfilm reading apparatus, to avoid useless image reading, since an abnormality for example in the light source can be securely detected, prior to the actual image reading from the microfilm. Besides an additional sensor for detecting the abnormality is not needed since the output of the linear sensor for image reading can be utilized for identification of abnormality.

Also, an exclusive circuit for detecting the abnormality is not needed, since the abnormality such as lamp failure can be identified by the histograms prepared for determining the threshold value for binary encoding.

Although the foregoing explanation has been limited to the image reading from a microfilm, the present invention is applicable also to other film reading apparatus such as that for reading a 35 mm film.

As explained in the foregoing, it is rendered possible to securely and effectively detect an abnormality in the light source for illuminating the film. Consequently, useless film reading operation can be avoided if the embodiment is applied to the detection of abnormality in the film illuminating light source of a film reading apparatus.

In the following there will be explained a method of detecting the image position, in the circuit shown in FIG. 2. FIG. 19 shows a flow chart of this operation, which is programmed in advance in the CPU 10. At first the linear sensor starts a reading operation for detecting the peak value, and the CPU 10 prepares histograms by fetching plural data of base density and peak value. Charts (1), (2) and (3) in FIG. 18 shown histograms in normal and image-free states in case of a negative film reading FIG. 18 (1) shows a case in which the image to be read is placed at a normal reading position, while FIG. 18 (2) shows a case in which the film is not leaded in the apparatus or the image is not placed at the reading position to allow light transmission though the film is loaded and FIG. 18 (3) shows a case in which the film is loaded in the apparatus but a totally black frame is placed at the reading position instead of the image.

Figure 18:
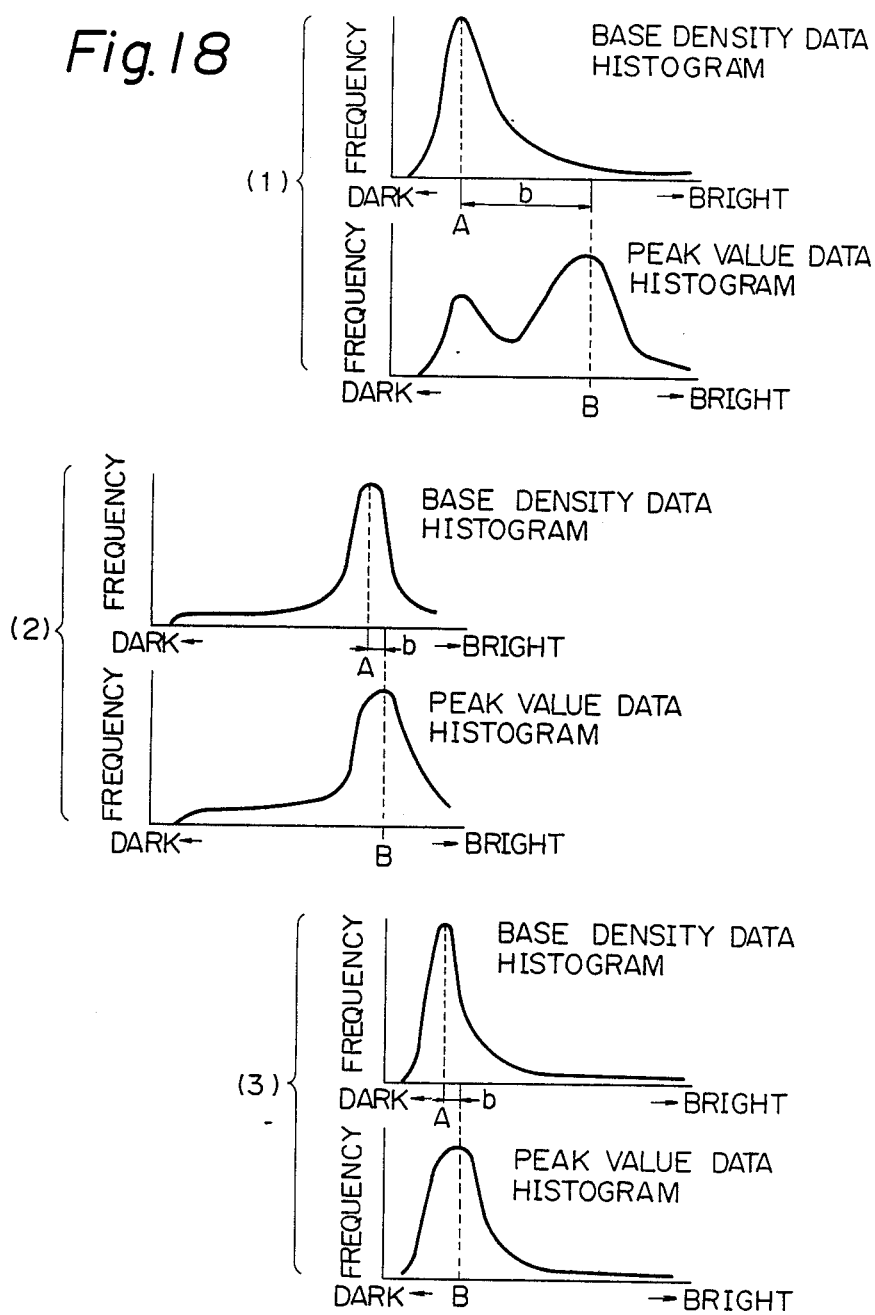
FIG. 18 is charts showing example of histograms relating to film position.
Figure 19:
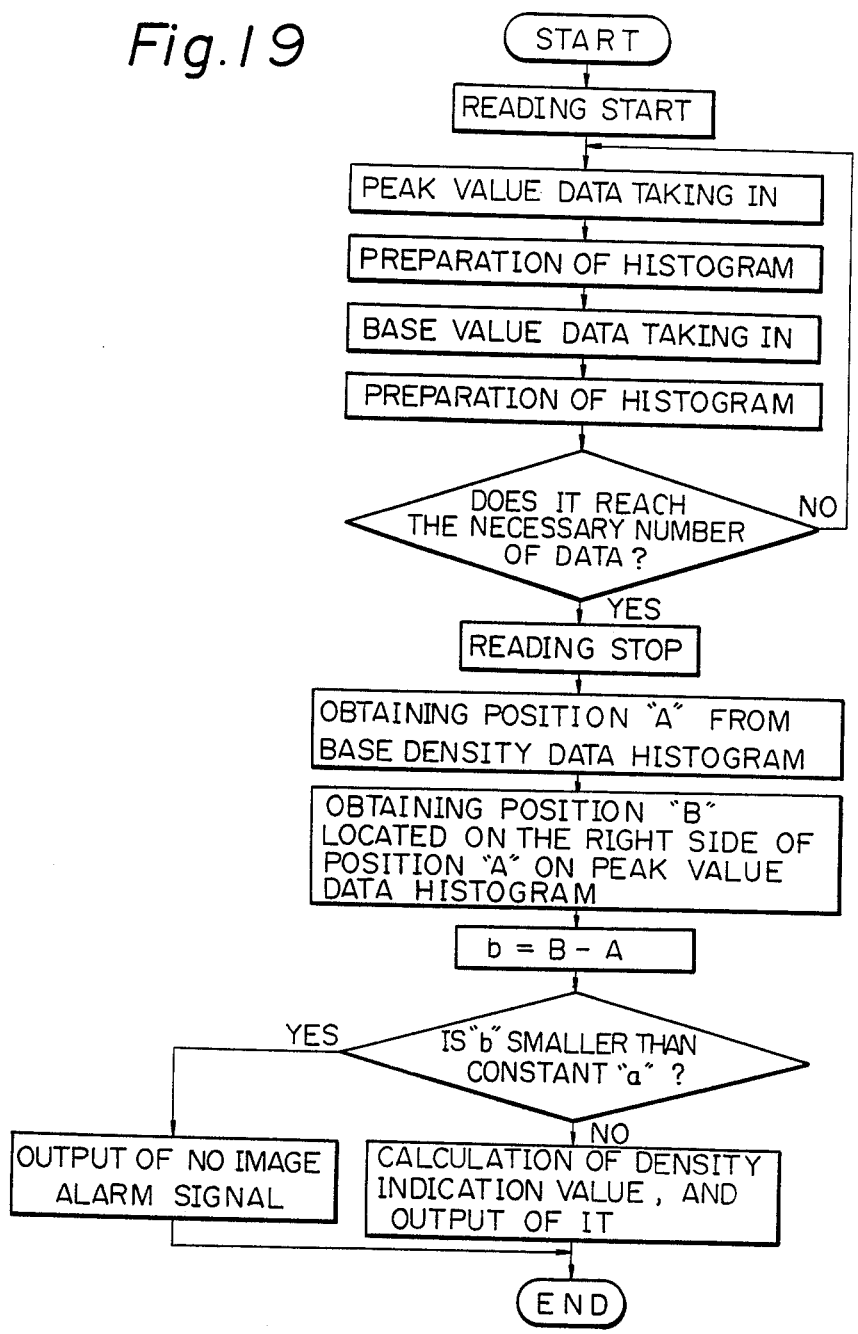
FIG. 19 is a flow chart showing the procedure of detecting a film position.

Referring to FIG. 18 (1), the contrast b specific to the image is given by b=B−A, wherein A is the peak position of the histogram of the base density in the normal state, while B is the right peak position of the histogram of the peak value. In a normal image, the contrast b is sufficiently large.

Referring to FIG. 18 (2) corresponding to a state in which the film is not loaded in the apparatus, or it is loaded but has not image in the reading position to allow light transmission, for example in a leader or trailer portion of the film, the peaks in both histograms are displaced to the right, and the value of contrast b is extremely small.

On the other hand, in the state of FIG. 18 (3) where the film is loaded but is totally black, thus lacking image, the peaks of both histograms are displaced to left (to a darker level), and the value of contrast b is again very small.

In this manner in the absence of image information, as shown in (2) or (3), the contrast b detected from the histograms become very small. Thus a non-image alarm signal can be released when the contrast b becomes smaller than a predetermined value.

Consequently the peak A of the histogram of the base density and the peak B at the lighter side of the histogram of the peak value are determined, and the difference b of said peaks is compared with a predetermined constant a. If the former is smaller, the CPU identifies the absence of the image in the appropriate reading position, and releases a non-image alarm signal to turn on the display unit 64. Said alarm signal may be utilized for interrupting the image reading or printing operation, or may be supplied to a host computer in case the microfilm reading apparatus is employed as an on-line terminal.

On the other hand, if the value b is larger, the CPU identifies that the microfilm image to be read is in the appropriate reading position, then releases a density instruction for determining the threshold value from the histograms of peak value and base density, executes the reading operation again with the linear sensor 2 and effects binary encoding of the obtained image signal with thus determined threshold value.

In this manner it is rendered possible to detect the position of the microfilm image, from the data distribution in the histograms prepared for determining the threshold value for binary encoding of the image signal.

The aforementioned constant a is regulated in consideration of statistical error and eventual fluctuation in the amount of light of the lamp.

Though the foregoing explanation has been limited to a case of reading a negative film, the detection of image position can also be achieved in a similar procedure in a positive film, since the normal histogram has an approximately the same distribution.

As explained in the foregoing, it is rendered possible, in a microfilm reading apparatus, to avoid useless image reading, since there can be identified whether the image is in the appropriate reading position, prior to the reading operation of the microfilm image. Also, there is not required a sensor for identifying the abnormality, since the detection is made on the basis of output of the linear sensor for image reading.

Furthermore, an exclusive circuit for identifying the abnormality is not required, since the image position is identified from the histograms formed for determining the threshold value for binary encoding.

Though the foregoing embodiment has been explained in relation to microfilm reading, it is also applicable to other film reading apparatus, for example for 35 mm film.

As explained in the foregoing, it is rendered possible to securely and effectively detect the position of the image to be illuminated by the light source. Consequently, useless image reading operation can be avoided if this embodiment is employed for identifying an abnormality in the light source for illuminating the film in the reading position.

Though the present invention has been explained by reference to the preferred embodiments, it is by no means limited to such embodiments but is subject to variations and modifications within the scope and spirit of the appended claims.

What is claimed is:

1. A film image reading apparatus comprising:
   means for illuminating a film on which an image is recorded;
   means for reading image recorded on the film illuminated by said illuminating means and for outputting image signals representing the image;
   first detection means for detecting an image density of the image recorded on the film on the basis of the image signals from said reading means;
   second detection means for detecting a base density of the film on the basis of the image signals from said reading means;
   means for quantizing the image signals outputted from said reading means; and
   means for determining a threshold value for quantizing the image signals on the basis of the thus detected image density and base density.

2. A film image reading apparatus according to claim 1, wherein said quantizing means is adapted to compare the image signals with the threshold value so as to generate binary image signals.

3. A film image reading apparatus according to claim 1, wherein said first detection means is adapted to detect the image density on the basis of a peak value of the image signals from said reading means.

4. A film image reading apparatus comprising:
   means for illuminating a film on which an image is recorded;
   means for reading line by line the image recorded on the film illuminated by said illuminating means and for outputting image signals representing the image;
   means for dividing the image signals of each reading line, outputting from said reading means, into plural blocks, each block including a predetermined amount of the image signals;
   means for detecting a respective peak value of the image signals in each block;
   means for quantizing the image signals outputted from said reading means; and
   means for determining a threshold value for quantizing the image signals on the basis of the the detected peak value of each blocks.

5. A film image reading apparatus according to claim 4, wherein said determining means is adapted to determine the threshold value on the basis of a frequency of the detected peak values.

6. A film image reading apparatus according to claim 4, wherein said detecting means is adapted to detect the peak value of image signals corresponding to a predetermined area of the film.

7. A film image reading apparatus comprising:
   means for illuminating a film on which an image is recorded;
   means for reading the image recorded on the film illuminated by said illuminating means and outputting image signals representing the image;
   means for detecting an image density of an image corresponding to a predetermined partial area of the film on the basis of the image signals from said reading means;
   means for quantizing the image signal outputted from said reading means; and
   means for determining a threshold value for quantizing the image signals on the basis of the detected density of an image.

8. A film image reading apparatus according to claim 7, wherein said quantizing means is adapted to compare the image signals with the threshold value so as to generate binary image signals.

9. A film image reading apparatus according to claim 7, wherein said detecting means is adapted to detect the image density on the basis of the peak value of the image signal outputted from said reading means.

10. A film image reading apparatus comprising:
    means for illuminating a film on which an image is recorded;
    means for reading the image recorded on the film illuminated by said illuminating means and outputting image signals representing the image;
    first detection means for detecting an output value of said reading means in a state where the film is not illuminated by said illuminating means;
    second detection means for detecting an image density of the image recorded on the film on the basis of the image signals from said reading means in a state where the film is illuminated by said illuminating means;
    means for quantizing the image signals outputted from said reading means; and
    means for determining a threshold value for quantizing the image signals on the basis of the thus detected output value and image density.

11. A film image reading apparatus according to claim 10, wherein said quantizing means is adapted to compare the image signals with the threshold value so as to generate a binary image signal.

12. A film image reading apparatus comprising:
    means for illuminating a film on which an image is recorded;
    means for reading the image recorded on the film illuminated by said illuminating means and for outputting image signals representing the image;
    first detection means for detecting a base density of the film on the basis of an output from said reading means when said reading means reads a non-image area of the film illuminated by said illuminating means; and
    means for determining the amount of light for said illuminating means according to the thus detected base density; and
    second detection means for detecting an image density of the image based on an output from said reading means when said reading means reads the image recorded on the film illuminated with the thus determined amount of light by said illuminating means.

13. A film image reading apparatus according to claim 12, wherein said second detection means is adapted to detect the image density on the basis of a peak value of the image signals from said reading means.

14. A film image reading apparatus comprising:
    means for illuminating a film on which an image is recorded;

means for reading the image recorded on the film illuminated by said illuminating means and for outputting image signals representing the image;

first detection means for detecting an image density of the image recorded on the film on the basis of the image signals from said reading means;

second detection means for detecting a base density of the film on the basis of the image signals from said reading means; and means for identifying an abnormality in said illuminating means on the basis of the thus detected image density and base density.

15. A film image reading apparatus according to claim 14, further comprising means for quantizing the image signals from said reading means on the basis of the thus detected image density and base density.

16. A film image reading apparatus according to claim 14, wherein said first detection means is adapted to detect the image density on the basis of a peak value of the image signals from said reading 17. A film image reading apparatus comprising:
means for illuminating a film on which an image is recorded;

means for reading the image recorded on the film illuminated by said illuminating means and for outputting image signals representing the image;

first detection means for detecting an image density of the image recorded on the film on the basis of an output from said reading means;

second detection means for detecting a base density of the film on the basis of an output from said reading means; and means for identifying the position of the image on the film on the basis of the thus detected image density and base density, to determine whether the image is proper or not proper for reading.

18. A film image reading apparatus according to claim 17, further comprising means for quantizing the image signals from said reading means on the basis of the thus detected image density and base density.

19. A film image reading apparatus according to claim 17, wherein said first detection means is adapted to detects the image density on the basis of a peak value of the image signals from said reading means.

20. A film image reading apparatus according to claim 1, wherein said first detection means is adapted to detect the image density of an image corresponding to a predetermined partial area of the film.

21. A film image reading apparatus according to claim 1, wherein said reading means comprises a linear image sensor capable of photoelectric conversion of light transmitted by a film.

22. A film image reading apparatus according to claim 1, further comprising means for moving a reading position on the film of said reading means.

23. A film image reading apparatus according to claim 1, further comprising means for displaying an enlarged image, which is an enlargement of the image recorded on the film.

24. A film image reading apparatus according to claim 4, wherein said quantizing means is adapted to compare the image signals with the threshold value so as to generate binary image signals.

25. A film image reading apparatus according to claim 4, further comprising second detecting means for detecting a base density of the film, wherein said determining means is adapted to determine the threshold value in consideration of the detected base density.

26. A film image reading apparatus according to claim 4, wherein said reading means comprises a linear image sensor capable of photoelectric conversion of light transmitted by a film.

27. A film image reading apparatus according to claim 4, further comprising means for moving a reading position of said reading means on the film.

28. A film image reading apparatus according to claim 4, further comprising means for displaying an enlarged image, which is an enlargement of the image recorded on the film.

29. A film image reading apparatus according to claim 7, further comprising second detecting means for detecting a base density of the film, wherein said determining means is adapted to determine the threshold value in consideration of the detected base density.

30. A film image reading apparatus according to claim 7, wherein said reading means comprises a linear image sensor capable of photoelectric conversion of light transmitted by a film.

31. A film image reading apparatus according to claim 7 further comprising means for moving a reading position of said reading means on the film.

32. A film image reading apparatus according to claim 7, further comprising means for displaying an enlarged image, which is an enlargement of the image recorded on the film.

33. A film image reading apparatus according to claim 7, wherein said first detection means comprise means for extracting the image signals representing the image corresponding to a predetermined partial area of the film.

34. A film image reading apparatus according to claim 10, wherein said second detection means is adapted to detect the image density on the basis of a peak value of the image signals from said reading means.

35. A film image reading apparatus according to claim 10, wherein said second detection means is adapted to detect the image density of an image corresponding to a predetermined partial area of the film.

36. A film image reading apparatus according to claim 10, further comprising third detection means for detecting a base density of the film, wherein said determining means is adapted to determine the threshold value in consideration of the detected base density.

37. A film image reading apparatus according to claim 10, wherein said reading means comprises a linear image sensor capable of photoelectric conversion of light transmitted by a film.

38. A film image reading apparatus according to claim 10, further comprising means for moving a reading position of said reading means on the film.

39. A film image reading apparatus according to claim 10, further comprising means for displaying an enlarged image, which is an enlargement of the image recorded on the film.

40. A film image reading apparatus according to claim 12, further comprising means for applying an electric power to said illuminating means in order to illuminate the film with the determine amount of light.

41. A film image reading apparatus according to claim 12, wherein said second detection means is adapted to detect the image density of an image corresponding to a predetermined partial area of the film.

42. A film image reading apparatus according to claim 12, further comprising means for quantizing the image signals outputted from said reading means and means for determining a threshold value for quantizing the image signals on the basis of the image density detected by said second detection means.

43. A film image reading apparatus according to claim 12, wherein said reading means comprises a linear image sensor capable of photoelectric conversion of light transmitted by a film.

44. A film image reading apparatus according to claim 12, further comprising means for moving a reading position of said reading means on the film.

45. A film image reading apparatus according to claim 12, further comprising means for displaying an enlarged image, which is an enlargement of the image recorded on the film.

46. A film image reading apparatus according to claim 14, wherein said identifying means is adapted to identify the abnormality in said illuminating means on the basis of a differential between the detected image density and the detected base density.

47. A film image reading apparatus according to claim 14, further comprising means for displaying a result of identification by said identifying means.

48. A film image reading apparatus according to claim 14, wherein said reading means comprises a linear image sensor capable of photoelectric conversion of light transmitted by a film.

49. A film image reading apparatus according to claim 14, further comprising means for moving a reading position of said reading means on the film.

50. A film image reading apparatus according to claim 14, further comprising means for displaying an enlarged image, which is an enlargement of the image recorded on the film.

51. A film image reading apparatus according to claim 17, wherein said identifying means is adapted to identify, whether or not the position of the image of the film is proper on the basis of a differential between the detected image density and the detected base density.

52. A film image reading apparatus according to claim 17, further comprising means for displaying a result of identification by said identifying means.

53. A film image reading apparatus according to claim 17, wherein said reading means comprises a linear image sensor capable of photoelectric conversion of light transmitted by a film.

54. A film image reading apparatus according to claim 17, further comprising means for moving a reading position of said reading means on the film.

55. A film image reading apparatus according to claim 17, further comprising means for displaying an enlarged image, which is an enlargement of the image recorded on the film.

56. A film image reading apparatus comprising:
means for illuminating a film on which an image is recorded;
means for reading the image recorded on the film illuminated by said illuminating means and for outputting image signals representing the image;
first detection means for detecting an image density of the image recorded on the film on the basis of the image signals form said reading means;
second detection means for detecting a base density of the film on the basis of the image signals from said reading means;
means for processing the image signals output from said reading means, for image reproduction; and
means for determining a parameter for processing the image signals on the basis of the thus detected image density and base density.

57. A film image reading apparatus according to claim 56, wherein said processing means comprises quantizing means for quantizing the image signals output from said reading means, and said determining means determines a threshold value for quantizing the image signals as the parameter.

58. A film image reading apparatus according to claim 57, wherein said quantizing means is adapted to compare the image signals with the threshold value to generate binary signals.

59. A film image reading apparatus according to claim 56, wherein said first detection means is adapted to detect the image density on the basis of a peak value of the image signals from said reading means.

60. A film image reading apparatus according to claim 56, wherein said first detection means is adapted to detect the image density of an image corresponding to a predetermined partial area of the film.

61. A film image reading apparatus according to claim 56, wherein said reading means comprises a linear image sensor capable of photoelectric conversion of light transmitted by the film.

62. A film image reading apparatus according to claim 56, further comprising means for moving a reading position on the film of said reading means.

63. A film image reading apparatus according to claim 56, further comprising means for displaying an enlarged image, which is an enlargement of the image recorded on the film.

64. A film image reading apparatus comprising:
means for illuminating a film on which an image is recorded;
means for reading line by line the image recorded on the film illuminated by said illuminating means and/or outputting image signals representing the image;
means for dividing the image signals of each reading line, output from said reading means, into plurality blocks, each block including a predetermined amount of the image signals;
means for detecting a respective peak value of the image signals in each block;
means for processing the image signals output from said reading means, for image reproduction; and
means for determining a parameter for processing the image signals on the basis of the detected peak value of each block.

65. A film image reading apparatus according to claim 64, wherein said processing means comprises quantizing means for quantizing the image signals output from said reading means, and said determining means determines a threshold value for quantizing the image signals as the parameter.

66. A film image reading apparatus according to claim 64, wherein said determining means is adapted to determine the parameter on the basis of the frequency of the detected peak values.

67. A film image reading apparatus according to claim 64, wherein said detecting means is adapted to detect the peak, value of image signals corresponding to a predetermined area of the film.

68. A film image reading apparatus according to claim 65, wherein said quantizing means is adapted to compare the image signals with the threshold value to generate binary image signals.

69. A film image reading apparatus according to claim 64, further comprising second detecting means for detecting a base density of the film, wherein said determining means is adapted to determine the parameter in consideration of the detected base density.

70. A film image reading apparatus according to claim 64, wherein said reading means comprises a linear image sensor capable of photoelectric conversion of light transmitted by the film.

71. A film image reading apparatus according to claim 64, further comprising means for moving a reading position of said reading means on the film.

72. A film image reading apparatus according to claim 64, further comprising means for displaying an enlarged image, which is an enlargement of the image recorded on the film.

73. A film image reading apparatus comprising:
means for illuminating a film on which an image is recorded;
means for reading the image recorded on the film illuminated by said illuminating means and outputting image signals representing the image;
means for detecting an image density of an image corresponding to as predetermined partial area of the film on the basis of the image signals from said reading means;
means for processing the image signal output from said reading means, for image reproduction; and
means for determining a parameter for processing the image signals on the basis of the detected density of an image.

74. A film image reading apparatus according to claim 73, wherein said processing means comprises quantizing means for quantizing the image signals output from said reading means, and said determining means determines a threshold value for quantizing the image signals as a parameter.

75. A film image reading apparatus according to claim 74, wherein said quantizing means is adapted to compare the image signals with the threshold value to generate binary image signals.

76. A film image reading apparatus according to claim 73, wherein said detecting means is adapted to detect the image density on the basis of the peak value of the image signal output from said reading means.

77. A film image reading apparatus according to claim 73, further comprising second detecting means for detecting a base density of the film, wherein said determining means is adapted to determine the parameter in consideration of the detected base density.

78. A film image reading apparatus according to claim 73, wherein said reading means comprises a linear image sensor capable of photoelectric conversion of light transmitted by the film.

79. A film image reading apparatus according to claim 73, further comprising means for moving a reading position of said reading means on the film.

80. A film image reading apparatus according to claim 73, further comprising means for displaying an enlarged image which is an enlargement of the image recorded on the film.

81. A film image reading apparatus according to claim 73, wherein said first detection means comprises means for extracting the image signals representing the image corresponding to a predetermined partial area of the film.

82. A film image reading apparatus comprising:
means for illuminating a film on which an image is recorded;
means for reading the image recorded on the film illuminated by said illuminating means and outputting image signals representing the image;
first detection means for detecting an output value of said reading means in a state where the film is not illuminated by said illuminating means;
second detection means for detecting an image density of the image record on the film on the basis of the image signals from said reading means in a state where the film is illuminated by said illuminating means;
means for processing the image signals output from said reading means, for image reproduction; and
means for determining a parameter for processing the image signals on the basis of the thus detected output value and image density.

83. A film image reading apparatus according to claim 82, wherein said processing means comprises quantizing means for quantizing the image signals output from said reading means, and said determining means determines a threshold value for quantizing the image signals as a parameter.

84. A film image reading apparatus according to claim 83, wherein said quantizing means is adapted to compare the image signals with the threshold value to generate a binary image signal.

85. A film image reading apparatus according claim 82, wherein said second detection means is adapted to detect the image density on the basis of a peak value of the image signals from said reading means.

86. A film image reading apparatus according to claim 82, wherein said second detection means is adapted to detect the image density of an image corresponding to a predetermined partial area of the film.

87. A film image reading apparatus according to claim 82, further comprising third detection means for detecting a base density of the film, wherein said determining means is adapted to determine the parameter in consideration of the detected base density.

88. A film image reading apparatus according to claim 82, wherein said reading means comprises a linear image sensor capable of photoelectric conversion of light transmitted by the film.

89. A film image reading apparatus according to claim 82, further comprising means for moving a reading position of said reading means on the film.

90. A film image reading apparatus according to claim 82, further comprising means for displaying an enlarged image which is an enlargement of the image recorded on the film.

* * * * *

UNITED STATES PATENT AND TRADEMARK OFFICE
CERTIFICATE OF CORRECTION

PATENT NO. : 4,837,450

DATED : June 6, 1989

INVENTOR(S) : Satomura et al.

It is certified that error appears in the above-identified patent and that said Letters Patent is hereby corrected as shown below:

COLUMN 1
  Line 19, delete "a".
  Line 57, delete "the" (second occurrence).

COLUMN 2
  Line 13, delete "to" (second occurrence).
  Line 45, change "to be" to --to provide a film exposing apparatus in which an image to be--.

COLUMN 3
  Line 55, change "14B" to --14B,--.
  Line 61, change "a charts" to --a set of charts--.
  Line 65, change "is charts" to --is a set of charts--.

COLUMN 4
  Line 8 change "is" to --are--.
  Line 14, change "charged-coupled" to --charge-coupled--.

COLUMN 5
  Line 18, delete "dividing".
  Line 34, change "suitable" to --suitably--.

COLUMN 8
  Line 16, change "yl(Dn'30 1-Dn)." to --yl(Dn'+1 - Dn)--.
  Line 32, change "PRISET" to --PRESET--.

UNITED STATES PATENT AND TRADEMARK OFFICE
CERTIFICATE OF CORRECTION

PATENT NO. : 4,837,450
DATED : June 6, 1989
INVENTOR(S) : Satomura et al.

It is certified that error appears in the above-identified patent and that said Letters Patent is hereby corrected as shown below:

COLUMN 9
  Line 44, change "$x_2$ (FIG. 11 (I))." to --$x_0$ (Fig. 11 (I)).--.

COLUMN 10
  Line 32, change "X'" to --$x_3$'--.

COLUMN 11
  Line 23, change "value $X_3$'0" --to value $X_3$'--.
  Line 57, change "Also" to --Also,--.
  Line 58, change "encoded" to --encoded,--.
  Line 64, change "the" to --a--.

COLUMN 12
  Line 23, change "circumferential" to --ambient--.
  Line 61, after "order to" insert --provide--.

COLUMN 14
  Line 46, delete "an".

COLUMN 15
  Line 12, change "image" to --the image--.
  Line 43, change "outputting" to --outputted--.
  Line 51, change "the the" to --the--.
  Line 52, change "each blocks." to --each block--.

COLUMN 16
  Line 50, delete "and".

UNITED STATES PATENT AND TRADEMARK OFFICE
CERTIFICATE OF CORRECTION

PATENT NO. : 4,837,450

DATED : June 6, 1989

INVENTOR(S) : Satomura et al.

It is certified that error appears in the above-identified patent and that said Letters Patent is hereby corrected as shown below:

COLUMN 17
   Line 20, change "reading" to --reading means--.
   Line 43, change "detects" to --detect--.

COLUMN 18
   Line 22, change "claim 7" to --claim 7,--.
   Line 29, change "comprise" to --comprises--.
   Line 61, change "determine" to --determined--.

COLUMN 19
   Line 63, change "form" to --from--.

COLUMN 20
   Line 41, change "plurality" to --a plurality of--.
   Line 63, change "peak," to --peak--.

COLUMN 21
   Line 25, change "as" to --a--.

UNITED STATES PATENT AND TRADEMARK OFFICE
CERTIFICATE OF CORRECTION

PATENT NO. : 4,837,450

DATED : June 6, 1989

INVENTOR(S) : Satomura et al.

It is certified that error appears in the above-identified patent and that said Letters Patent is hereby corrected as shown below:

COLUMN 22

Line 18, change "record" to --recorded--.

Signed and Sealed this

Twenty-fourth Day of July, 1990

Attest:

HARRY F. MANBECK, JR.

Attesting Officer

Commissioner of Patents and Trademarks